United States Patent
Cocker et al.

(10) Patent No.: US 8,747,356 B2
(45) Date of Patent: Jun. 10, 2014

(54) FLUID DELIVERY SYSTEM WITH MULTI-DOSE FLUID SOURCE

(75) Inventors: Robin C. Cocker, Oldham (GB); Paul A. Johnson, Columbia, MD (US)

(73) Assignee: Mallinckrodt LLC, Hazelwood, MO (US)

( * ) Notice: Subject to any disclaimer, the term of this patent is extended or adjusted under 35 U.S.C. 154(b) by 0 days.

(21) Appl. No.: 12/742,928

(22) PCT Filed: Nov. 19, 2008

(86) PCT No.: PCT/US2008/012894
§ 371 (c)(1),
(2), (4) Date: May 14, 2010

(87) PCT Pub. No.: WO2009/067200
PCT Pub. Date: May 28, 2009

(65) Prior Publication Data
US 2010/0249586 A1    Sep. 30, 2010

Related U.S. Application Data

(60) Provisional application No. 60/988,858, filed on Nov. 19, 2007.

(51) Int. Cl.
*A61B 18/14* (2006.01)
*A61M 39/00* (2006.01)

(52) U.S. Cl.
USPC .......................................... 604/114; 604/533

(58) Field of Classification Search
USPC .................... 604/113, 114, 154, 181, 187
See application file for complete search history.

(56) References Cited

U.S. PATENT DOCUMENTS

| | | | |
|---|---|---|---|
| 1,961,023 A | | 5/1934 | West |
| 4,416,663 A | | 11/1983 | Hall |
| 4,728,496 A | | 3/1988 | Petersen et al. |
| 5,037,395 A | * | 8/1991 | Spencer ..................... 604/113 |
| 5,116,652 A | | 5/1992 | Alzner |
| 5,328,463 A | | 7/1994 | Barton et al. |
| 5,342,320 A | | 8/1994 | Cameron |
| 5,353,691 A | | 10/1994 | Haber et al. |
| 5,356,375 A | | 10/1994 | Higley |
| 5,423,751 A | | 6/1995 | Harrison et al. |

(Continued)

FOREIGN PATENT DOCUMENTS

| | | |
|---|---|---|
| CN | 2063018 | 10/1990 |
| JP | 4-500622 | 2/1992 |

(Continued)

*Primary Examiner* — Aarti B Berdichevsky

(57) ABSTRACT

A fluid delivery system (400A) is generally directed to allowing fluid sources or other fluid delivery components to be reused with multiple fluid targets (318), and includes at least one fluid source (314) fluidly interconnectable with at least one sterilization zone (316) and at least one fluid target (318). This sterilization zone (316) could include one or more sterilization systems that attempt to neutralize contaminants entering the fluid delivery system (400A) by a backflow from the fluid target (318). One such sterilization system (500A-D) includes a container (502a-d) and a flush system (520) for sterilizing the container (502a-d) between uses. Another sterilization system (600) includes a flowpath (604) exposed to an output of an energy source (602) capable of destroying contaminants. Yet another sterilization system could include a sterilizing substance (710) that engages and moves along an interior surface (705) of a housing (704) to treat contamination thereon.

17 Claims, 16 Drawing Sheets

(56) References Cited

U.S. PATENT DOCUMENTS

| | | | |
|---|---|---|---|
| 5,569,181 | A | 10/1996 | Heilman et al. |
| 5,569,208 | A | 10/1996 | Woelpper et al. |
| 5,586,975 | A | 12/1996 | Tanaka et al. |
| 5,921,759 | A | 7/1999 | Khan |
| 6,142,977 | A | 11/2000 | Kolberg et al. |
| 6,187,400 | B1 | 2/2001 | Woo et al. |
| 6,596,230 | B1 | 7/2003 | Woo et al. |
| 6,623,455 | B2 | 9/2003 | Small et al. |
| 6,626,862 | B1 | 9/2003 | Duchon et al. |
| 6,650,929 | B1 | 11/2003 | Nemoto et al. |
| 6,706,020 | B1 | 3/2004 | Urich |
| 6,731,971 | B2 | 5/2004 | Evans, III et al. |
| 6,872,197 | B1 | 3/2005 | Witowski |
| 6,972,001 | B2 | 12/2005 | Emig et al. |
| 7,153,285 | B2 * | 12/2006 | Lauman et al. ............ 604/6.08 |
| 7,156,824 | B2 * | 1/2007 | Rosenman ................. 604/113 |
| 7,267,666 | B1 | 9/2007 | Duchon et al. |
| 7,458,951 | B2 * | 12/2008 | Lauman et al. ............ 604/6.08 |
| 7,500,961 | B2 * | 3/2009 | Nemoto ................... 604/151 |
| 2001/0009994 | A1 | 7/2001 | Small et al. |
| 2002/0143294 | A1 | 10/2002 | Duchon et al. |
| 2003/0135250 | A1 | 7/2003 | Lauman et al. |
| 2004/0002685 | A1 | 1/2004 | Patzer |
| 2004/0092885 | A1 | 5/2004 | Duchon et al. |
| 2004/0254525 | A1 | 12/2004 | Uber, III et al. |
| 2004/0260143 | A1 | 12/2004 | Reilly et al. |
| 2005/0004447 | A1 | 1/2005 | Yamamoto |
| 2005/0148934 | A1 | 7/2005 | Martens et al. |
| 2005/0234428 | A1 | 10/2005 | Spohn et al. |
| 2006/0074350 | A1 | 4/2006 | Cash |
| 2006/0151049 | A1 * | 7/2006 | Nemoto ................... 141/27 |
| 2006/0184122 | A1 * | 8/2006 | Nemoto ................... 604/154 |
| 2007/0142774 | A1 * | 6/2007 | Rosenman ................ 604/113 |
| 2007/0167919 | A1 * | 7/2007 | Nemoto et al. ........... 604/189 |
| 2008/0021393 | A1 * | 1/2008 | Gill et al. ................. 604/113 |
| 2008/0086094 | A1 | 4/2008 | Peters |
| 2008/0281268 | A1 * | 11/2008 | Vest Hansen ............. 604/114 |
| 2009/0194168 | A1 | 8/2009 | Liepold |

FOREIGN PATENT DOCUMENTS

| | | |
|---|---|---|
| JP | 5-329209 | 12/1993 |
| JP | 2006230739 | 9/2006 |
| WO | 2005110007 | 11/2005 |
| WO | WO 2007/030630 | 3/2007 |
| WO | WO 2007/116086 | 10/2007 |

* cited by examiner

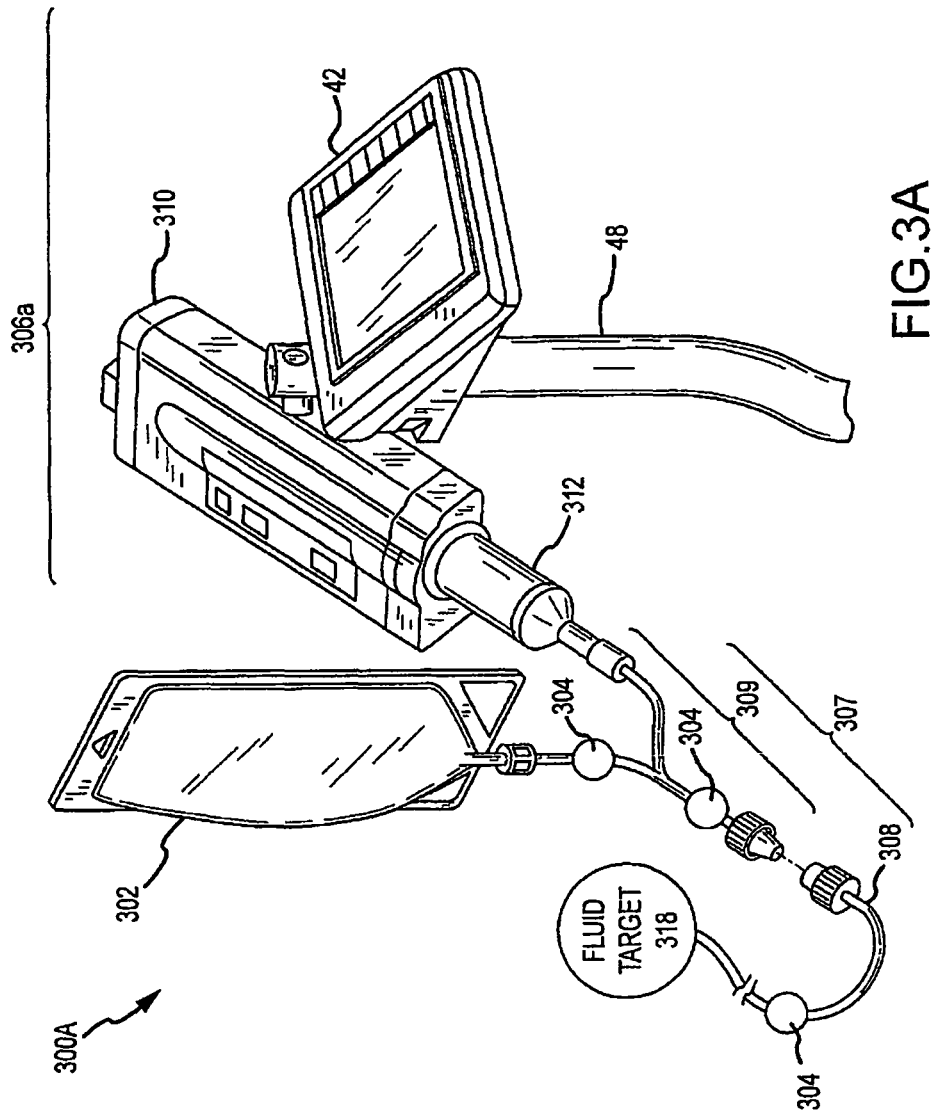

FLUID DELIVERY SYSTEM WITH MULTI-DOSE FLUID SOURCE

CROSS-REFERENCE TO RELATED APPLICATIONS

This patent application is a U.S. National Stage of PCT/US2008/012894, filed on Nov. 19, 2008, which claims priority to U.S. Provisional Patent Application Ser. No. 60/988,858, that is entitled "FLUID DELIVERY SYSTEM WITH MULTI-DOSE FLUID SOURCE," and that was filed on Nov. 19, 2007.

FIELD OF THE INVENTION

The present invention generally relates to the field of fluid delivery systems and, more particularly, to incorporating one or more sterilization zones in a fluid delivery system that accommodates using a multi-dose fluid source.

BACKGROUND

Medical contrast media is a relatively expensive product. Factory pre-filled syringes or vials may be used to transport individual contrast media doses to the point of use. In this case, it is common for a certain amount of contrast media to be left after an injection procedure (e.g., based upon differences between patients, differences between imaging requirements, or both). Any remaining contrast media is typically disposed of as waste. It has at least been suggested to utilize a bulk storage container of contrast media that may be used to supply contrast media for multiple injection procedures. Since contrast media tends to be a parenteral drug, and since contamination may be introduced into the fluid delivery system when fluidly connected with a patient, sterilization may be a concern when using a multi-dose contrast media source for multiple patients.

SUMMARY

The present invention is generally directed to providing a sterilization function in relation to the delivery of a fluid. First and second aspects of the present invention are generally directed to providing a sterilization function utilizing an energy source output. Third and fourth aspects of the present invention are generally directed to providing a sterilization function utilizing an intermediate chamber or container somewhere between a fluid source and a fluid target. Fifth and sixth aspects of the present invention are generally directed to providing a sterilization function utilizing a "wiping action" or the like of a surface that is exposed to fluid, where the surface that is exposed to fluid that may be delivered to a patient, and where the wiping action is provided by a sterilizing element or medium. Each of these various aspects will now be addressed in more detail.

A first aspect of the present invention is embodied by a fluid delivery system having a fluid reservoir, an injector, and an energy source. A first flowpath extends from the fluid source to a fluid target. The injector is at least fluidly interconnectable with the first flowpath. At least part of the first flowpath is exposed to an output from the energy source. This exposure may be utilized to at least reduce the contamination level of fluid passing through the first flowpath (e.g., to reduce the potential for contaminants migrating from the fluid target back to the fluid reservoir and/or the injector).

Various refinements exist of the features noted in relation to the first aspect of the present invention. Further features may also be incorporated in the first aspect of the present invention as well. These refinements and additional features may exist individually or in any combination. The following discussion, up to the introduction of a second aspect of the present invention, pertains to this first aspect.

The first flowpath may be defined in any appropriate manner, for instance in the form of or otherwise defined by at least one conduit. Each conduit may be of any appropriate size, shape, configuration, and/or type (e.g., medical tubing). In one embodiment, the first flowpath includes first and second conduit sections that are detachably interconnected in any appropriate manner, with the first conduit section extending from the second conduit section to the fluid target, with the first conduit section being in the form of a disposable, and with the second conduit section being reusable for multiple fluid delivery procedures (e.g., for use with a number of fluid targets). At least part of the first conduit section may be exposed to the output of the energy source.

The energy source may be of any appropriate size, shape, configuration, and/or type. One embodiment has the energy source being in the form of a heater. Another embodiment has the energy source being in the form of a radiation source that emits radiation at one or more wavelengths. Having at least about 5 inches or 13 centimeters of the first conduit section exposed to the output from the energy source may further reduce the potential of contaminants from the fluid target being able to migrate back through the fluid delivery system to the fluid reservoir and/or the injector.

A second aspect of the present invention is embodied by a method for delivering fluid. A flowpath extends from a fluid reservoir to a first fluid target. Fluid is stored in a fluid reservoir, and at least some of this fluid is discharged or released from the fluid reservoir. A first dose of fluid from that which has been discharged from the fluid reservoir is delivered to the first fluid target via the noted flowpath. At least part of the flowpath is exposed to an energy source output (e.g., to reduce the potential for contaminants migrating from the first fluid target back to the fluid reservoir).

Various refinements exist of the features noted in relation to the second aspect of the present invention. Further features may also be incorporated in the second aspect of the present invention as well. These refinements and additional features may exist individually or in any combination. The following discussion, up to the introduction of a third aspect of the present invention, pertains to this second aspect. The output from the energy source may be of any appropriate type or combination of types. The energy source output to which at least part of the flowpath is exposed may be in the form of radiation (e.g., gamma radiation). Radiation of any appropriate wavelength or combination of wavelengths may be utilized (e.g., ultraviolet light, infrared light). Heat may also be utilized as the energy source output, and this heat may be generated in any appropriate manner. One embodiment entails heating fluid within the exposed portion of the flowpath to a temperature of at least about 104° F. or 40° C.

The length of the flowpath that is exposed to an energy source output may be selected to further reduce the potential of contaminants being able to proceed through the exposure zone to reach the fluid reservoir. In one embodiment, one or more aspects of the energy source output (e.g., the dose or dose rate), along with the length of the flowpath to be exposed to the energy source output, may be selected so as to significantly reduce the potential of a contaminant being able to proceed entirely through this exposed portion of the flowpath. In one embodiment, the length of the flowpath that is exposed to the energy source output is at least about 5 inches or 13 centimeters.

One of the benefits associating with exposing at least part of the flowpath to an energy source output is that the fluid reservoir may contain a sufficient quantity of fluid so as to be usable for multiple fluid targets and/or multiple fluid delivery procedures. In one embodiment, the first fluid target is disconnected from the fluid reservoir (e.g., physically and/or fluidly). At least some of the fluid within the fluid reservoir is discharged or released from the fluid reservoir. A second fluid target is connected to the fluid reservoir. A second dose of fluid from that which has been discharged from the fluid reservoir is delivered to the second fluid target. Any appropriate sequence may be utilized in relation to this delivery of a second dose of fluid to the second fluid target. For instance, fluid for the second dose may be discharged or released from the fluid reservoir after the first fluid target has been disconnected (e.g., physically and/or fluidly) from the fluid reservoir. The second fluid target may be connected to the fluid reservoir after the first fluid target has been disconnected from the fluid reservoir.

A third aspect of the present invention is embodied by a fluid delivery system having a fluid reservoir, a first container, an injector, and a flush system, where the injector is not part of the flush system. The first container may be fluidly interconnected with the fluid reservoir, the injector may be fluidly interconnected with at least one of the fluid reservoir and the first container, and the flush system may be fluidly interconnected with the first container. The injector may be operated to direct a flow through a conduit to a fluid target.

Various refinements exist of the features noted in relation to the third aspect of the present invention. Further features may also be incorporated in the third aspect of the present invention as well. These refinements and additional features may exist individually or in any combination. The following discussion, up to the introduction of a fourth aspect of the present invention, pertains to this third aspect. The flush system may be in the form of a flush source and a flush receptacle, each of which may be of any appropriate size, shape, configuration, and/or type. For instance, the flush source may utilize a single flushing medium or a combination of two or more flushing mediums of any appropriate form, where each flushing medium may provide any appropriate function or combination of functions (e.g., sterilization). Representative flushing mediums include without limitation alcohol, steam, ETO (ethylene oxide), a sterilizing fluid, water, air, an inert gas or combination of inert gases, bleach, hydrogen peroxide, oxygen, and any combination thereof. The flush receptacle may be in the form of any appropriate container, storage vessel, or the like, or may simply be in the form of a drain or the like.

The fluid reservoir may be selectively fluidly interconnected with and fluidly isolated from the first container in any appropriate manner. The first container may be selectively fluidly interconnected with and fluidly isolated from the flush source in any appropriate manner. The fluid target may be selectively fluidly interconnected with and fluidly isolated from the first container in any appropriate manner. The flush receptacle may be selectively fluidly interconnected with and fluidly isolated from the first container in any appropriate manner. For instance, one or more valves (e.g., check valves, throttle valves, gate valves, solenoid valves), flow control devices, or the like may be utilized in relation to providing the desired "state" of fluid communication between the above-noted pairs of structures.

A number of configurations exist for directing a flushing medium both into and out of the first container (e.g., to provide a sterilizing function). Stated another way, the flush system may be integrated with the fluid delivery system in various manners. Representative integrations of a flush system will now be addressed.

In a first embodiment, the first container includes a first inlet port and a first outlet port, where the fluid reservoir and the flush source each may be fluidly interconnected with the first inlet port, and where the fluid target and flush receptacle each may be fluidly interconnected with the first outlet port. Both the fluid reservoir and flush source could remain physically interconnected with the first container through the first inlet port, and yet could be either fluidly isolated from or fluidly connected to the first container (e.g., via one or more valves, flow control devices, or the like). The first inlet port could also be physically disconnected from the fluid reservoir and physically connected to the flush source, to fluidly isolate and fluidly interconnect, respectively, these structures, and vice versa. Similarly, both the fluid target and flush receptacle could remain physically interconnected with the first container through the first outlet port, and yet could be either fluidly isolated from or fluidly connected to the first container (e.g., via one or more valves, flow control devices, or the like). The first outlet port could also be physically disconnected from the fluid target and physically connected to the flush receptacle, to fluidly isolate and fluidly interconnect, respectively, these structures, and vice versa. Each of the fluid reservoir, the fluid target, the flush source, and the flush receptacle may be fluidly interconnected with and fluidly isolated from the first container in any appropriate manner. In any case, at least one flushing medium may be directed into the first container from the flush source through the first inlet port, while the fluid reservoir and fluid target are each fluidly isolated from the first container. Flushing medium may be directed out of the first container and into the flush receptacle through the first outlet port, while the fluid reservoir and fluid target are each fluidly isolated from the first container.

In a second embodiment, the first container includes first and second inlet ports, along with a first outlet port. The first inlet port is fluidly interconnectable with the fluid reservoir, while the second inlet port is fluidly interconnectable with the flush source. Both the fluid target and the flush receptacle may be fluidly interconnected with the first outlet port. The fluid target and flush receptacle could remain physically interconnected with the first container through the first outlet port, and yet could be either fluidly isolated from or fluidly connected to the first container (e.g., via one or more valves, flow control devices, or the like). The first outlet port could also be physically disconnected from the fluid target and physically connected to the flush receptacle, to fluidly isolate and fluidly interconnect, respectively, these structures, and vice versa. Each of the fluid reservoir, the fluid target, the flush source, and the flush receptacle may be fluidly interconnected with and fluidly isolated from the first container in any appropriate manner. In any case, at least one flushing medium may be directed into the first container from the flush source through the second inlet port, while the fluid reservoir and fluid target are each fluidly isolated from the first container. Flushing medium may be directed out of the first container and into the flush receptacle through the first outlet port, while the fluid reservoir and fluid target are each fluidly isolated from the first container.

In a third embodiment, the first container includes first and second inlet ports, as well as first and second outlet ports. The first inlet port may be fluidly interconnected with the fluid reservoir, while the second inlet port may be fluidly interconnected with the flush source. The first outlet port may be fluidly interconnected with the fluid target, while the second outlet port may be fluidly interconnected with the flush receptacle. The second inlet port and second outlet port may be characterized as flushing ports. Each of the fluid reservoir, the fluid target, the flush source, and the flush receptacle may be fluidly interconnected with and fluidly isolated from the first container in any appropriate manner. In any case, at least one flushing medium may be directed into the first container from the flush source through the second inlet port, while the fluid reservoir and fluid target are each fluidly isolated from the first container. Flushing medium may be directed out of the first container and into the flush receptacle through the second outlet port, while the fluid reservoir and fluid target are each fluidly isolated from the first container.

In a fourth embodiment, the first container includes a first inlet port, a first outlet port, and a flushing port, where the fluid reservoir may be fluidly interconnected with the first inlet port, where the fluid target may be fluidly interconnected with the first outlet port, and where each of the flush source and flush receptacle may be fluidly interconnected with the flushing port. Each of the fluid reservoir, the fluid target, the flush source, and the flush receptacle may be fluidly interconnected with and fluidly isolated from the first container in any appropriate manner. In any case, at least one flushing medium may be directed into the first container from the flush source through the flushing port, while the fluid reservoir and fluid target are each fluidly isolated from the first container. Flushing medium may be directed out of the first container through the first flushing port and into the flush receptacle, while the fluid reservoir and fluid target are each fluidly isolated from the first container.

Any appropriate function or combination of functions may be provided by a flushing of the first container. Any appropriate number of flushes of the first container may be undertaken. In one embodiment and after the first container has been sterilized, clean water and/or air/inert gas may be used to flush the first container. The first container may be sterilized in any appropriate manner, such as by flushing the first container with an appropriate sterilizing medium, by exposing the first container to an output of an energy source (e.g., heat, gamma radiation, ultraviolet light, infrared light, and any combination thereof), or both. In the second instance, the first container may be sterilized without its interior surfaces being physically contacted.

A fourth aspect of the present invention is embodied by a method for delivering fluid. A first fluid quantity is directed from a fluid reservoir into a first container. A first dose is delivered to a first fluid target, where the first dose is at least part of the first fluid quantity. After the first dose has been retrieved or discharged from the first container, at least some of any of the original first fluid quantity that remains in the first container may be removed from the first container (e.g., an attempt may be made to "drain" the first container). A second fluid quantity is directed from the fluid reservoir into the first container. A second dose is delivered to a second fluid target, where the second dose is at least part of the second fluid quantity. Therefore, the fourth aspect encompasses the successive delivery of fluid to multiple fluid targets.

Various refinements exist of the features noted in relation to the fourth aspect of the present invention. Further features may also be incorporated in the fourth aspect of the present invention as well. These refinements and additional features may exist individually or in any combination. The following discussion, up to the introduction of a fifth aspect of the present invention, pertains to this fourth aspect. The first fluid quantity in the second fluid quantity may be of the same or different amounts. The first dose and the second dose may be of the same or different amounts. The first dose may be any portion of the first fluid quantity, including being the entirety of the first fluid quantity. The second dose may be any portion of the second fluid quantity, including being the entirety of the second fluid quantity.

Any remainder of the first fluid quantity within the first container, where the remainder is that which may remain within the first container after the first dose has been removed from the first container, may be removed from the first container in any appropriate manner. At least some of this remainder may be withdrawn from the first container and directed back into the fluid reservoir. The first container may include an outlet port that is fluidly interconnectable with the first fluid target, and the first fluid target may be disconnected from or at least fluidly isolated from this outlet port such that at least some of the remainder may be discharged from the first container through this outlet port without proceeding to the first fluid target. The first container may include an outlet port that is fluidly interconnectable with the first fluid target, along with a separate bleed port (e.g., a second outlet port) that may be utilized to at least partially drain the first container. An appropriate fluid may be directed through the first container to remove any remainder of the first fluid quantity. Any appropriate combination of the foregoing may be utilized to attempt to "drain" the first container.

The first container may be flushed in any appropriate manner after at least some of any remainder of the first fluid quantity has been removed or drained from the first container (e.g., in accordance with the third aspect). Any flushing of the first container may provide any appropriate function or combination of functions in the manner discussed above in relation to the third aspect. The first container may also be sterilized in the manner discussed above in relation to the third aspect (e.g., flushing and/or exposing the first container to an energy source output).

A flushing medium may be directed through the first container, where the first container remains physically interconnected with each of the fluid reservoir in the first fluid target, and without having any of this flushing medium proceed to either the fluid reservoir or the first fluid target. The fluid reservoir and the first fluid target each may be fluidly isolated from the first container, and thereafter a flushing medium may be introduced into and discharged from the first container. In a first embodiment, the fluid reservoir is fluidly isolated from an inlet port of the first container and the first fluid target is fluidly isolated from an outlet port of the first container, and thereafter a flushing medium is introduced into and discharged from the first container through the inlet and outlet ports, respectively. In a second embodiment, the fluid reservoir is fluidly isolated from a first inlet port of the first container and the first fluid target is fluidly isolated from an outlet port of the first container, and thereafter a flushing medium is introduced into and discharged from the first container through a second inlet port and the outlet port, respectively. In a third embodiment, the fluid reservoir is fluidly isolated from an inlet port of the first container and the first fluid target is fluidly isolated from an outlet port of the first container, and thereafter a flushing medium is introduced into and discharged from the first container through first and second flushing ports, respectively. In a fourth embodiment, the fluid reservoir is fluidly isolated from an inlet port of the first container and the first fluid target is fluidly isolated from an outlet port of the first container, and thereafter a flushing medium is introduced into and discharged from the first container through a common flushing port.

A fifth aspect of the present invention is embodied by what may be characterized as a flow control device. This flow control device includes a housing and a plunger. At least part of the plunger is movably disposed within the housing. First and second seals are mounted on and spaced along the plunger, and furthermore engage an interior surface of the housing. A first sterilizing substance is contained between the first and second seals.

Various refinements exist of the features noted in relation to the fifth aspect of the present invention. Further features may also be incorporated in the fifth aspect of the present invention as well. These refinements and additional features may exist individually or in any combination. The following discussion, up to the introduction of a sixth aspect of the present invention, pertains to this fifth aspect. The flow control device may be incorporated by a fluid delivery system that includes a fluid reservoir. Fluid from this fluid reservoir may be directed to the flow control device. A discharge or output from the flow control device may be directed to a fluid target. In one embodiment, the flow control device is of the "pass through" type in relation to a fluid flow from a fluid reservoir.

The first and second seals may be many appropriate size, shape, configuration, and/or type. In one embodiment, the first and second seals are in the form of O-rings. Any appropriate spacing between the first and second seals may be utilized. The first and second seals may move along with the plunger relative to the housing. As such, the first sterilizing substance that is retained between the first and second seals may move along with the plunger relative to the housing as well. Moving the first sterilizing substance along the interior surface of the housing may "wipe" an engaged portion of the interior surface to address contamination.

The first sterilizing substance may engage the interior surface of the housing. The phrase "engaging the interior surface of the housing" or the like encompasses engaging any portion of the interior surface, and including engaging the entirety of the interior surface. The first sterilizing substance may be of any appropriate type and/or form. The first sterilizing substance may be in the form of a sterilizing liquid, a solid or other carrier that is impregnated with or that contains a sterilizing liquid. A sterilizing substance may be incorporated by or integrated with a sponge, cloth, a porous material, a hydrophilic material, and any combination thereof.

The flow control device may be in the form of a syringe. In this case, the housing may be in the form of a syringe barrel and at least part of the plunger may be disposed within the syringe barrel. The plunger may extend beyond an end of the syringe barrel and may be hand-activated. Another option is for the syringe to be adapted for use with a power injector, where a drive of the power injector may be interconnected with the plunger in any appropriate manner to move the plunger relative to the syringe barrel (e.g., to provide a fluid discharge from the syringe barrel).

The flow control device may include at least one biasing member that is engaged with the plunger. Any such biasing member may be of any appropriate size, shape, configuration, and/or type. Any appropriate number of biasing members may be utilized. In one embodiment, the plunger is biased away from an open position for the flow control device (e.g., an "open" position being one that allow flow through the flow control device), and toward a closed position for the flow control device (e.g., a "closed" position being one that does not allow flow through the flow control device). For instance, the plunger may be biased to a position that does not accommodate a flow out of the flow control device.

Third and fourth seals may be mounted on and spaced along the plunger. The third and fourth seals may engage an interior surface of the housing, and a second sterilizing substance may be contained between the third and fourth seals. The features discussed above in relation to the first sterilizing substance are equally applicable to the second sterilizing substance. Although the first and second sterilizing substances may be the same, such need not be the case. The third and fourth seals may move along with the plunger relative to the housing. As such, the second sterilizing substance that is retained between the third and fourth seals may move along with the plunger relative to the housing as well. Moving the second sterilizing substance along the interior surface of the housing may "wipe" an engaged portion of the interior surface to address contamination.

The first and second seals may define a first seal pair, while the above-noted third and fourth seals may define a second seal pair. The first and second seal pairs may be spaced any appropriate distance along the plunger. In one embodiment and with the plunger being in position where there is no flow out of the flow control device, the first seal pair may be at least generally disposed toward or at an inlet to the flow control device and the second seal pair may be disposed at least generally toward or at an outlet of the flow control device.

The housing may include first and second flow passages that may be in selective fluid communication. In one embodiment, the first and second flow passages may be fluidly isolated from each other when the plunger is in a first position (e.g., a closed position for the flow control device, where there is no flow out of the flow control device). In one embodiment, the first and second passages may be in fluid communication when the plunger is in a second position (e.g., an open position for the flow control device, where there is a flow out of the flow control device).

A fifth seal may be mounted on the plunger at a location that is between the above-noted first and second seal pairs, and where this fifth seal is engageable with the interior surface of the housing. Any appropriate spacing between the fifth seal and each of the first and second seal pairs may be utilized. This fifth seal may block fluid communication between the above-noted first and second flow passages when the plunger is in a first position (e.g., a closed position for the flow control device, where there is no flow out of the flow control device). Moving the plunger to a second position may establish fluid communication between the first and second flow passages (e.g., an open position for the flow control device, where there is a flow out of the flow control device). That is, moving the plunger to the second position may move the fifth seal so that it no longer is disposed between the first and second flow passages to establish a fluid communication therebetween.

The flow control device may include a cap that is detachably or removably engaged with the housing. This cap may be removed to allow the flow control device to be fluidly interconnected with another structure, such as a connector that is fluidly interconnectable with a fluid target. This connector may be part of a tubing set or the like that extends from the flow control device to a fluid target (e.g., a patient).

The above-noted connector may be detachably or removably interconnected with the housing in any appropriate manner, such as by a threaded engagement. The connector may include a third flow passage. Interconnecting the connector with the flow control device may fluidly interconnect the above-noted first and second flow passages of the flow control device with the third flow passage of the connector. In one embodiment, the connector includes a first member of any appropriate configuration (e.g., a second, stationary plunger of sorts). The third flow passage may extend from a sidewall to an interior portion of the first member. Sixth and seventh seals may be mounted on and spaced along the first member at a location such that third flow passage intersects with the sidewall of the first member at a location between these sixth and seventh seals.

The above-noted connector may utilize any appropriate cover or cap (e.g., a peel-off strip or the like). This cover or cap may be removed when the connector is being interconnected with the flow control device. The first member of the connector may be directed into the interior of the flow control device, such that the above-noted sixth and seventh seals engage the interior surface of the housing. Advancing the connector relative to the housing may bring the first member of the connector into engagement with the plunger such that the plunger is moved from a "closed position" to an "open position" where flow proceeds through the flow control device, into the connector, and then to a fluid target (e.g., via tubing on which the connector is mounted). For instance, installing the connector to the flow control device may establish fluid communication between the above-noted first and second flow passages of the flow control device, and may also establish fluid communication between the third flow passage of the connector and the first and second flow passages of the flow control device.

A sixth aspect of the present invention is embodied by a method for delivering fluid. Fluid may be provided to a flow control device, where this flow control device includes a housing having an interior surface that defines at least part of a conduit. A sterilizing element may be moved along at least part of the interior surface. Fluid may be discharged from the flow control device. At least some fluid that is discharged from the flow control device will flow through a portion of the conduit that was contacted by the sterilizing element.

Various refinements exist of the features noted in relation to the sixth aspect of the present invention. Further features may also be incorporated in the sixth aspect of the present invention as well. These refinements and additional features may exist individually or in any combination. The following discussion pertains to this sixth aspect unless otherwise noted. Fluid may be provided to the flow control device in any appropriate manner. In one embodiment, the flow control device is in the form of a syringe, and fluid may be loaded into this syringe in any appropriate manner. In one embodiment, fluid is provided to the flow control device by fluidly interconnecting the flow control device with a fluid reservoir. This fluid reservoir may contain multiple fluid doses, for instance for multiple fluid targets. A first fluid dose may be retrieved from the fluid reservoir, loaded into and/or passed through the flow control device, and discharged from the flow control device (e.g., to a first fluid target). A second fluid dose may be retrieved from the fluid reservoir after the first fluid dose has been discharged from the flow control device, loaded into and/or passed through the flow control device, and discharged from the flow control device (e.g., to a second fluid target). It should be appreciated that the entire first and second fluid dose need not be contained within the flow control device at any one time.

The sterilizing element may be mounted on a plunger that is disposed within the conduit. The plunger may be moved within the conduit in any appropriate manner, which in turn may move the sterilizing element along the interior surface of the conduit. The sterilizing element may be characterized as being movable at least generally between first and second positions, and where the flow control device may be characterized as having a flowpath that extends through the flow control device and that includes at least the above-noted conduit. At least part of the flowpath through the flow control device may be blocked with the sterilizing element being in its first position, whereas the flowpath through the flow control device may be open with the sterilizing element being in its second position. In one embodiment, at least part of the flow control device is biased to a position where at least part of the flowpath is blocked.

A first fluid target may be fluidly interconnected with the flow control device. A movement of the first sterilizing element may be responsive to or caused by the establishment of a fluid interconnection between the first fluid target and the flow control device. After fluid has been provided to the first fluid target through the flow control device, the first fluid target may be disconnected from the flow control device. This disconnection may cause the sterilizing element to move relative to the conduit. The sterilizing element may move to a position that is associated with terminating a fluid output from the flow control device. In any case and subsequent to the disconnection of the first fluid target from the flow control device, a second fluid target may be fluidly interconnected with the flow control device. The fluidly interconnecting the second fluid target with the flow control device may again move the sterilizing element relative to the conduit. Once a sufficient interconnection exists between the second fluid target and the flow control device, fluid may exit the flow control device and be directed toward the second fluid target. In one embodiment, fluid provided from the flow control device to each of the first and second fluid targets is received from a common fluid reservoir.

A target side connector may be coupled with the flow control device, and the target side connector may be fluidly interconnectable with a fluid target. An open end of the target side connector may be sealed prior to being engaged with the flow control device. An open end of the flow control device may be sealed prior to being engaged with the target side connector. Each of these seals may be removed such that the target side connector and flow control device may be coupled. Coupling the target side connector and the flow control device may cause the sterilizing element to move relative to the conduit associated with the flow control device.

Various refinements exist of the features noted in relation to each of the above-noted first through the sixth aspects of the present invention. Further features may also be incorporated in each of the above-noted first through the sixth aspects of the present invention as well. These refinements and additional features may exist individually or in any desired combination in relation to each of the first through the sixth aspects. That is, each of the following features that will be discussed is not required to be used with any other feature or combination of features unless otherwise specified.

Any fluid reservoir that is utilized may be of any size, shape, configuration, and/or type. Multiple fluid reservoirs may be utilized as well. Any appropriate fluid may be stored within any fluid reservoir that is being utilized, including without limitation contrast media, a radiopharmaceutical, saline, and any combination thereof. In one embodiment, multiple fluid doses are stored in the fluid reservoir. A "dose" may be in the form of a predetermined fluid quantity that is intended to be delivered to each of multiple fluid targets. Each dose may or may not be of the same fluid quantity.

Any fluid target may be of any appropriate size, shape, configuration, and/or type. One embodiment has the fluid target being in the form of a patient. Another embodiment has the fluid target being in the form of an animal. In any case, fluid may be delivered in any appropriate manner to a fluid target. For instance, fluid may be injected into a particular fluid target. Fluid may also be topically delivered to a particular fluid target.

An injector may be used to create a fluid flow to a fluid target, and this injector may be of any appropriate size, shape, configuration, and/or type. One embodiment has the injector being in the form of a hand-operated unit (e.g., a manually operable syringe). Another embodiment has the injector being in the form of a power injector (e.g., a syringe that is interconnectable with and driven by operation of a powerhead). Multiple injectors could also be utilized and disposed in any appropriate arrangement.

Any power injector may be of any appropriate size, shape, configuration, and/or type. Any such power injector may utilize one or more syringe plunger drivers of any appropriate size, shape, configuration, and/or type, where each such syringe plunger driver is capable of at least bi-directional movement (e.g., a movement in a first direction for discharging fluid; a movement in a second direction for accommodating a loading of fluid or so as return to a position for a subsequent fluid discharge operation). The power injector may be used for any appropriate application where the delivery of one or more fluids is desired and in any appropriate manner (e.g., via injection into a fluid target such as a patient), including without limitation any appropriate medical application (e.g., computed tomography or CT imaging; magnetic resonance imaging or MRI; SPECT imaging; PET imaging; X-ray imaging; angiographic imaging; optical imaging; ultrasound imaging). The power injector may be used in conjunction with any component or combination of components, such as an appropriate imaging system (e.g., a CT scanner). For instance, information could be conveyed between the power injector and one or more other components (e.g., scan delay information, injection start signal, injection rate). Any appropriate number of syringes may be integrated with the power injector in any appropriate manner (e.g., detachably; front-loaded; rear-loaded; side-loaded), any appropriate fluid may be discharged from a given syringe of the power injector, and any appropriate fluid may be discharged from a multiple syringe power injector configuration in any appropriate manner (e.g., sequentially, simultaneously), or any combination thereof. In one embodiment, fluid discharged from a syringe by operation of the power injector is directed into a conduit, where this conduit is fluidly interconnected with the syringe in any appropriate manner and directs fluid to a desired location (e.g., to a patient, for instance for injection).

BRIEF DESCRIPTION OF THE FIGURES

FIG. 3A is a perspective view of one embodiment of a fluid delivery system that utilizes a power injector.

DETAILED DESCRIPTION

Figure 1:
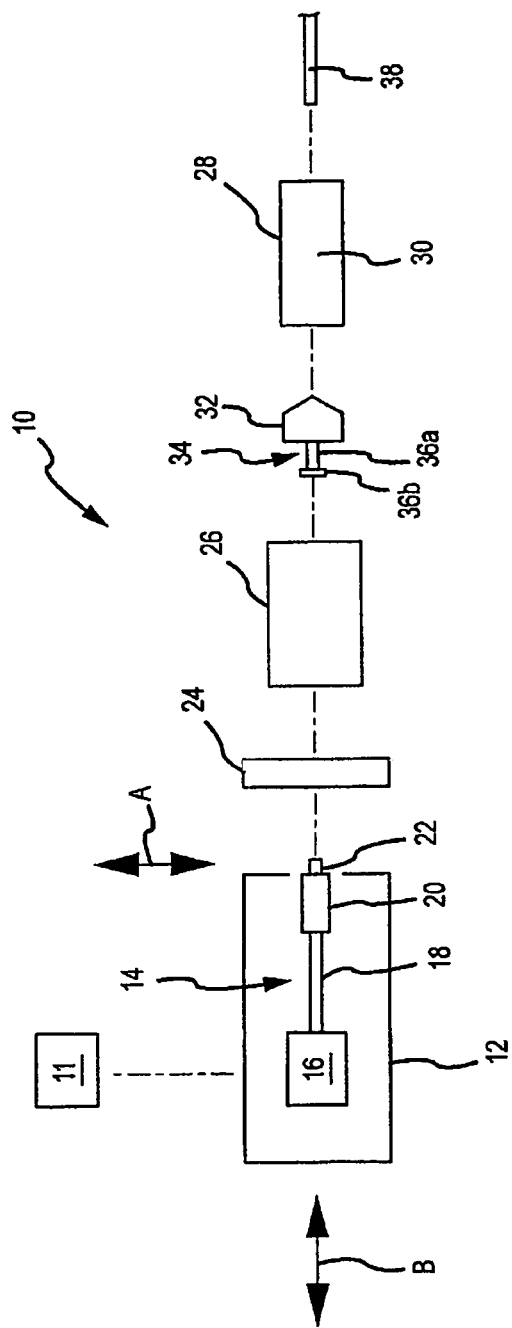
FIG. 1 is a schematic of one embodiment of a power injector.

FIG. 1 presents a schematic of one embodiment of a power injector 10 having a powerhead 12. One or more graphical user interfaces or GUIs 11 may be associated with the powerhead 12. Each GUI 11: 1) may be of any appropriate size, shape, configuration, and/or type; 2) may be operatively interconnected with the powerhead 12 in any appropriate manner; 3) may be disposed at any appropriate location; 4) may be configured to provide one or any combination of the following functions: controlling one or more aspects of the operation of the power injector 10; inputting/editing one or more parameters associated with the operation of the power injector 10; and displaying appropriate information (e.g., associated with the operation of the power injector 10); or 5) any combination of the foregoing. Any appropriate number of GUIs 11 may be utilized. In one embodiment, the power injector 10 includes a GUI 11 that is incorporated by a console that is separate from but which communicates with the powerhead 12. In another embodiment, the power injector 10 includes a GUI 11 that is part of the powerhead 12. In yet another embodiment, the power injector 10 utilizes one GUI 11 on a separate console that communicates with the powerhead 12, and also utilizes another GUI 11 that is on the powerhead 12. Each GUI 11 could provide the same functionality or set of functionalities, or the GUIs 11 may differ in at least some respect in relation to their respective functionalities.

A syringe 28 may be installed on this powerhead 12 and may be considered to be part of the power injector 10. Some injection procedures may result in a relatively high pressure being generated within the syringe 28. In this regard, it may be desirable to dispose the syringe 28 within a pressure jacket 26. The pressure jacket 26 is typically installed on the powerhead 12, followed by disposing the syringe 28 within the pressure jacket 26. The same pressure jacket 26 will typically remain installed on the powerhead 12, as various syringes 28 are positioned within and removed from the pressure jacket 26 for multiple injection procedures. The power injector 10 may eliminate the pressure jacket 26 if the power injector 10 is configured/utilized for low-pressure injections. In any case, fluid discharged from the syringe 28 may be directed into a conduit 38 of any appropriate size, shape, configuration, and/or type, which may be fluidly interconnected with the syringe 28 in any appropriate manner, and which may direct fluid to any appropriate location (e.g., to a patient).

The powerhead 12 includes a syringe plunger drive assembly 14 that interfaces with the syringe 28 to discharge fluid from the syringe 28. This syringe plunger drive assembly 14 includes a drive source 16 (e.g., a motor of any appropriate size, shape, configuration, and/or type, optional gearing, and the like) that powers a drive output 18 (e.g., a rotatable drive screw). A ram 20 may be advanced along an appropriate path (e.g., axial) by the drive output 18. The ram 20 may include a coupler 22 for interfacing with a corresponding portion of the syringe 28 in a manner that will be discussed below.

The syringe 28 includes a plunger or piston 32 that is movably disposed within a syringe barrel 30 (e.g., for axial reciprocation along an axis coinciding with the double-headed arrow B). The plunger 32 may include a coupler 34. This syringe plunger coupler 34 may interconnect with the ram coupler 22 to allow the syringe plunger drive assembly 14 to retract the syringe plunger 32 within the syringe barrel 30. The syringe plunger coupler 34 may be in the form of a shaft 36a that extends from a body of the syringe plunger 32, together with a head or button 36b. However, the syringe plunger coupler 34 may be of any appropriate size, shape, configuration, and/or type.

Retraction of the syringe plunger 32 may be utilized to accommodate a loading of fluid into the syringe barrel 30 for a subsequent injection or discharge, may be utilized to actually draw fluid into the syringe barrel 30 for a subsequent injection or discharge, or for any other appropriate purpose. Certain configurations may not require that the syringe plunger drive assembly 14 be able to retract the syringe plunger 32, in which case the ram coupler 22 and syringe plunger coupler 34 may not be required. Even when a ram coupler 22 and syringe plunger coupler 34 are utilized, it may such that these components may or may not be coupled when the ram 20 advances the syringe plunger 32 to discharge fluid from the syringe 28 (e.g., the ram 20 may simply push on the syringe plunger coupler 34 or on a proximal end of the syringe plunger 32). Any single motion or combination of motions in any appropriate dimension or combination of dimensions may be utilized to dispose the ram coupler 22 and syringe plunger coupler 34 in a coupled state or condition, to dispose the ram coupler 22 and syringe plunger coupler 34 in an un-coupled state or condition, or both.

The syringe 28 may be installed on the powerhead 12 in any appropriate manner. For instance, the syringe 28 could be configured to be installed directly on the powerhead 12. In the illustrated embodiment, a housing 24 is appropriately mounted on the powerhead 12 to provide an interface between the syringe 28 and the powerhead 12. This housing 24 may be in the form of an adapter to which one or more configurations of syringes 28 may be installed, and where at least one configuration for a syringe 28 could be installed directly on the powerhead 12 without using any such adapter. The housing 24 may also be in the form of a faceplate to which one or more configurations of syringes 28 may be installed. In this case, it may be such that a faceplate is required to install a syringe 28 on the powerhead 12—the syringe 28 could not be installed on the powerhead 12 without the faceplate. When a pressure jacket 26 is being used, it may be installed on the powerhead 12 in the various manners discussed herein in relation to the syringe 28, and the syringe 28 will then thereafter be installed in the pressure jacket 26.

The housing 24 may be mounted on and remain in a fixed position relative to the powerhead 12 when installing a syringe 28. Another option is to movably interconnect the housing 24 and the powerhead 12 to accommodate installing a syringe 28. For instance, the housing 24 may move within a plane that contains the double-headed arrow A to provide one or more of coupled state or condition and an un-coupled state or condition between the ram coupler 22 and the syringe plunger coupler 34.

Figure 2A:
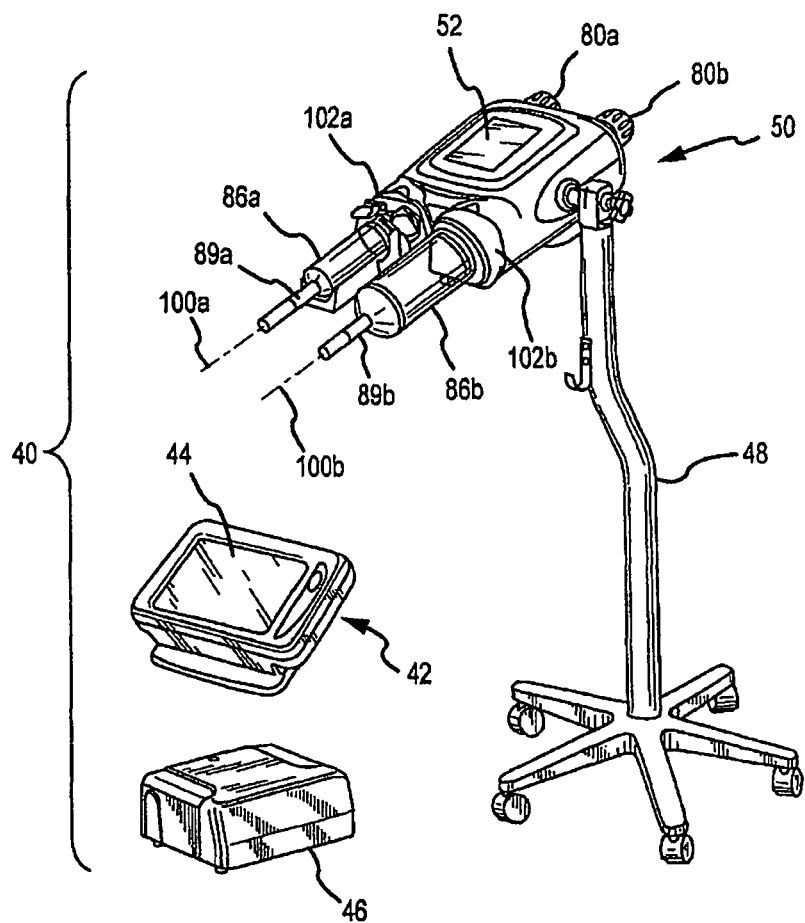
FIG. 2A is a perspective view of one embodiment of a portable stand-mounted, dual-head power injector.

One particular power injector configuration is illustrated in FIG. 2A, is identified by a reference numeral 40, and is at least generally in accordance with the power injector 10 of FIG. 1. The power injector 40 includes a powerhead 50 that is mounted on a portable stand 48. A pair of syringes 86a, 86b for the power injector 40 are mounted on the powerhead 50. Fluid may be discharged from the syringes 86a, 86b during operation of the power injector 40.

The portable stand 48 may be of any appropriate size, shape, configuration, and/or type. Wheels, rollers, casters, or the like may be utilized to make the stand 48 portable. The powerhead 50 could be maintained in a fixed position relative to the portable stand 48. However, it may be desirable to allow the position of the powerhead 50 to be adjustable relative to the portable stand 48 in at least some manner. For instance, it may be desirable to have the powerhead 50 in one position relative to the portable stand 48 when loading fluid into one or more of the syringes 86a, 86b, and to have the powerhead 50 in a different position relative to the portable stand 48 for performance of an injection procedure. In this regard, the powerhead 50 may be movably interconnected with the portable stand 48 in any appropriate manner (e.g., such that the powerhead 50 may be pivoted through at least a certain range of motion, and thereafter maintained in the desired position).

It should be appreciated that the powerhead 50 could be supported in any appropriate manner for providing fluid. For instance, instead of being mounted on a portable structure, the powerhead 50 could be interconnected with a support assembly, that in turn is mounted to an appropriate structure (e.g., ceiling, wall, floor). Any support assembly for the powerhead 50 may be positionally adjustable in at least some respect (e.g., by having one or more support sections that may be repositioned relative to one more other support sections), or may be maintained in a fixed position. Moreover, the powerhead 50 may be integrated with any such support assembly so as to either be maintained in a fixed position or so as to be adjustable relative the support assembly.

The powerhead 50 includes a graphical user interface or GUI 52. This GUI 52 may be configured to provide one or any combination of the following functions: controlling one or more aspects of the operation of the power injector 40; inputting/editing one or more parameters associated with the operation of the power injector 40; and displaying appropriate information (e.g., associated with the operation of the power injector 40). The power injector 40 may also include a console 42 and powerpack 46 that each may be in communication with the powerhead 50 in any appropriate manner (e.g., via one or more cables), that may be placed on a table or mounted on an electronics rack in an examination room or at any other appropriate location, or both. The powerpack 46 may include one or more of the following and in any appropriate combination: a power supply for the injector 40; interface circuitry for providing communication between the console 42 and powerhead 50; circuitry for permitting connection of the power injector 40 to remote units such as remote consoles, remote hand or foot control switches, or other original equipment manufacturer (OEM) remote control connections (e.g., to allow for the operation of power injector 40 to be synchronized with the x-ray exposure of an imaging system); and any other appropriate componentry. The console 42 may include a touch screen display 44, which in turn may provide one or more of the following functions and in any appropriate combination: allowing an operator to remotely control one or more aspects of the operation of the power injector 40; allowing an operator to enter/edit one or more parameters associated with the operation of the power injector 40; allowing an operator to specify and store programs for automated operation of the power injector 40 (which can later be automatically executed by the power injector 40 upon initiation by the operator); and displaying any appropriate information relation to the power injector 40 and including any aspect of its operation.

Figure 2B:
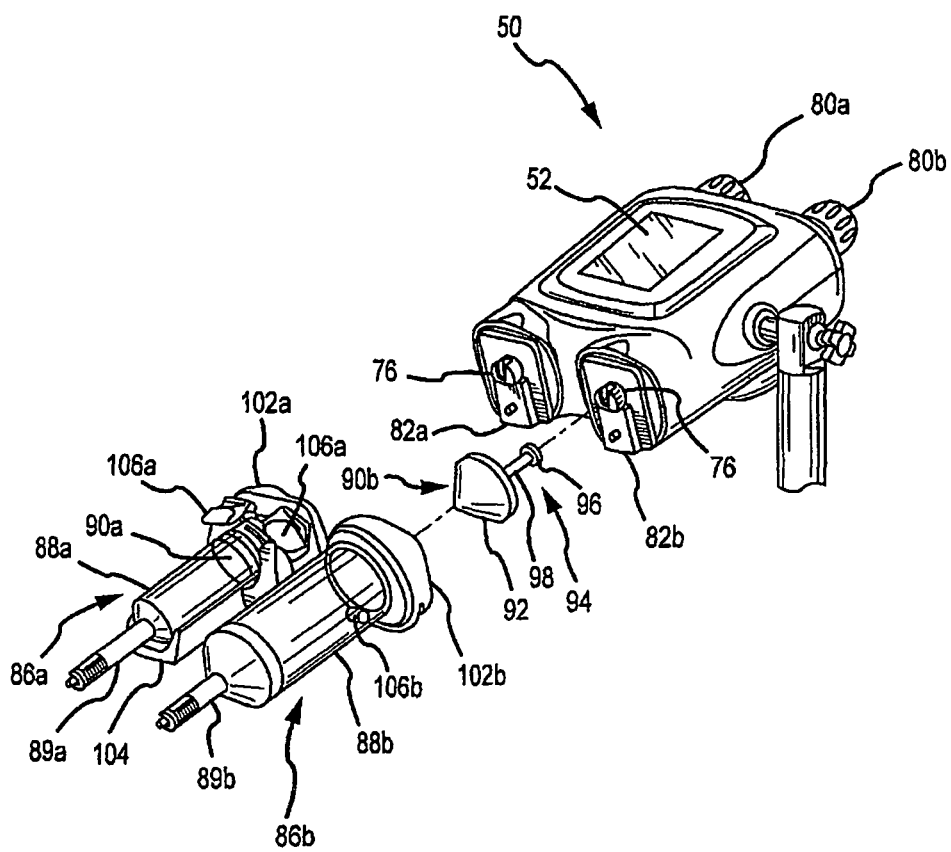
FIG. 2B is an enlarged, partially exploded, perspective view of a powerhead used by the power injector of FIG. 2A.

Various details regarding the integration of the syringes 86*a*, 86*b* with the powerhead 50 are presented in FIG. 2B. Each of the syringes 86*a*, 86*b* includes the same general components. The syringe 86*a* includes plunger or piston 90*a* that is movably disposed within a syringe barrel 88*a*. Movement of the plunger 90*a* along an axis 100*a* (FIG. 2A) via operation of the powerhead 50 will discharge fluid from within the syringe barrel 88*a* through a nozzle 89*a* of the syringe 86*a*. An appropriate conduit (not shown) will typically be fluidly interconnected with the nozzle 89*a* in any appropriate manner to direct fluid to a desired location (e.g., a patient). Similarly, the syringe 86*b* includes plunger or piston 90*b* that is movably disposed within a syringe barrel 88*b*. Movement of the plunger 90*b* along an axis 100*b* (FIG. 2A) via operation of the powerhead 50 will discharge fluid from within the syringe barrel 88*b* through a nozzle 89*b* of the syringe 86*b*. An appropriate conduit (not shown) will typically be fluidly interconnected with the nozzle 89*b* in any appropriate manner to direct fluid to a desired location (e.g., a patient).

The syringe 86*a* is interconnected with the powerhead 50 via an intermediate faceplate 102*a*. This faceplate 102*a* includes a cradle 104 that supports at least part of the syringe barrel 88*a*, and which may provide/accommodate any additional functionality or combination of functionalities. A mounting 82*a* is disposed on and is fixed relative to the powerhead 50 for interfacing with the faceplate 102*a*. A ram coupler 76 of a ram 74, which are each part of a syringe plunger drive assembly 56 for the syringe 86*a*, is positioned in proximity to the faceplate 102*a* when mounted on the powerhead 50. Details regarding the syringe plunger drive assembly 56 will be discussed in more detail below in relation to FIG. 2C. Generally, the ram coupler 76 may be coupled with the syringe plunger 90*a* of the syringe 86*a*, and the ram coupler 76 and ram 74 may then be moved relative to the powerhead 50 to move the syringe plunger 90*a* along the axis 100*a* (FIG. 2A). It may be such that the ram coupler 76 is engaged with, but not actually coupled to, the syringe plunger 90*a* when moving the syringe plunger 90*a* to discharge fluid through the nozzle 89*a* of the syringe 86*a*.

The faceplate 102*a* may be moved at least generally within a plane that is orthogonal to the axes 100*a*, 100*b* (associated with movement of the syringe plungers 90*a*, 90*b*, respectively, and illustrated in FIG. 2A), both to mount the faceplate 102*a* on and remove the faceplate 102*a* from its mounting 82*a* on the powerhead 50. The faceplate 102*a* may be used to couple the syringe plunger 90*a* with its corresponding ram coupler 76 on the powerhead 50. In this regard, the faceplate 102*a* includes a pair of handles 106*a*. Generally and with the syringe 86*a* being initially positioned within the faceplate 102*a*, the handles 106*a* may be moved to in turn move/translate the syringe 86*a* at least generally within a plane that is orthogonal to the axes 100*a*, 100*b* (associated with movement of the syringe plungers 90*a*, 90*b*, respectively, and illustrated in FIG. 2A). Moving the handles 106*a* to one position moves/translates the syringe 86*a* (relative to the faceplate 102*a*) in an at least generally downward direction to couple its syringe plunger 90*a* with its corresponding ram coupler 76. Moving the handles 106*a* to another position moves/translates the syringe 86*a* (relative to the faceplate 102*a*) in an at least generally upward direction to uncouple its syringe plunger 90*a* from its corresponding ram coupler 76.

The syringe 86*b* is interconnected with the powerhead 50 via an intermediate faceplate 102*b*. A mounting 82*b* is disposed on and is fixed relative to the powerhead 50 for interfacing with the faceplate 102*b*. A ram coupler 76 of a ram 74, which are each part of a syringe plunger drive assembly 56 for the syringe 86*b*, is positioned in proximity to the faceplate 102*b* when mounted to the powerhead 50. Details regarding the syringe plunger drive assembly 56 again will be discussed in more detail below in relation to FIG. 2C. Generally, the ram coupler 76 may be coupled with the syringe plunger 90*b* of the syringe 86*b*, and the ram coupler 76 and ram 74 may be moved relative to the powerhead 50 to move the syringe plunger 90*b* along the axis 100*b* (FIG. 2A). It may be such that the ram coupler 76 is engaged with, but not actually coupled to, the syringe plunger 90*b* when moving the syringe plunger 90*b* to discharge fluid through the nozzle 89*b* of the syringe 86*b*.

The faceplate 102*b* may be moved at least generally within a plane that is orthogonal to the axes 100*a*, 100*b* (associated with movement of the syringe plungers 90*a*, 90*b*, respectively, and illustrated in FIG. 2A), both to mount the faceplate 102*b* on and remove the faceplate 102*b* from its mounting 82*b* on the powerhead 50. The faceplate 102*b* also may be used to couple the syringe plunger 90*b* with its corresponding ram coupler 76 on the powerhead 50. In this regard, the faceplate 102*b* may include a handle 106*b*. Generally and with the syringe 86*b* being initially positioned within the faceplate 102*b*, the syringe 86*b* may be rotated along its long axis 100*b* (FIG. 2A) and relative to the faceplate 102*b*. This rotation may be realized by moving the handle 106*b*, by grasping and turning the syringe 86*b*, or both. In any case, this rotation moves/translates both the syringe 86*b* and the faceplate 102*b* at least generally within a plane that is orthogonal to the axes 100*a*, 100*b* (associated with movement of the syringe plungers 90*a*, 90*b*, respectively, and illustrated in FIG. 2A). Rotating the syringe 86*b* in one direction moves/translates the syringe 86*b* and faceplate 102*b* in an at least generally downward direction to couple the syringe plunger 90*b* with its corresponding ram coupler 76. Rotating the syringe 86*b* in the opposite direction moves/translates the syringe 86*b* and faceplate 102*b* in an at least generally upward direction to uncouple its syringe plunger 90*b* from its corresponding ram coupler 76.

As illustrated in FIG. 2B, the syringe plunger 90*b* includes a plunger body 92 and a syringe plunger coupler 94. This syringe plunger coupler 94 includes a shaft 98 that extends from the plunger body 92, along with a head 96 that is spaced from the plunger body 92. Each of the ram couplers 76 includes a larger slot that is positioned behind a smaller slot on the face of the ram coupler 76. The head 96 of the syringe plunger coupler 94 may be positioned within the larger slot of the ram coupler 76, and the shaft 98 of the syringe plunger coupler 94 may extend through the smaller slot on the face of the ram coupler 76 when the syringe plunger 90b and its corresponding ram coupler 76 are in a coupled state or condition. The syringe plunger 90a may include a similar syringe plunger coupler 94 for interfacing with its corresponding ram coupler 76.

Figure 2C:
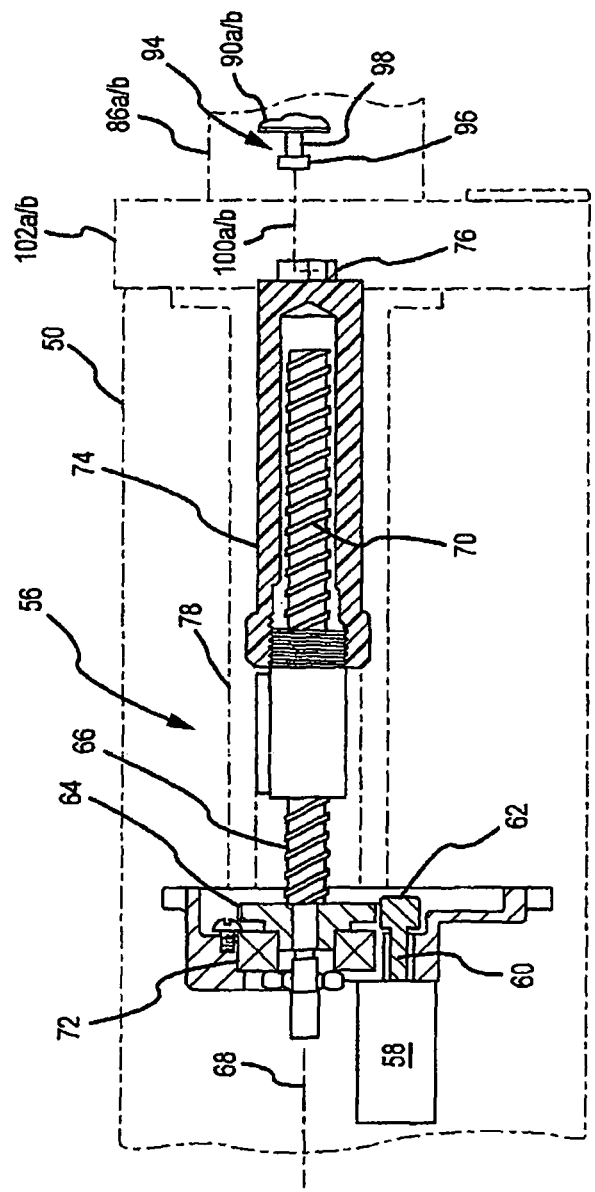
FIG. 2C is a schematic of one embodiment of a syringe plunger drive assembly used by the power injector of FIG. 2A.

The powerhead 50 is utilized to discharge fluid from the syringes 86a, 86b in the case of the power injector 40. That is, the powerhead 50 provides the motive force to discharge fluid from each of the syringes 86a, 86b. One embodiment of what may be characterized as a syringe plunger drive assembly is illustrated in FIG. 2C, is identified by reference numeral 56, and may be utilized by the powerhead 50 to discharge fluid from each of the syringes 86a, 86b. A separate syringe plunger drive assembly 56 may be incorporated into the powerhead 50 for each of the syringes 86a, 86b. In this regard and referring back to FIGS. 2A-B, the powerhead 50 may include hand-operated knobs 80a and 80b for use in separately controlling each of the syringe plunger drive assemblies 56.

Initially and in relation to the syringe plunger drive assembly 56 of FIG. 2C, each of its individual components may be of any appropriate size, shape, configuration and/or type. The syringe plunger drive assembly 56 includes a motor 58, which has an output shaft 60. A drive gear 62 is mounted on and rotates with the output shaft 60 of the motor 58. The drive gear 62 is engaged or is at least engageable with a driven gear 64. This driven gear 64 is mounted on and rotates with a drive screw or shaft 66. The axis about which the drive screw 66 rotates is identified by reference numeral 68. One or more bearings 72 appropriately support the drive screw 66.

A carriage or ram 74 is movably mounted on the drive screw 66. Generally, rotation of the drive screw 66 in one direction axially advances the ram 74 along the drive screw 66 (and thereby along axis 68) in the direction of the corresponding syringe 86a/b, while rotation of the drive screw 66 in the opposite direction axially advances the ram 74 along the drive screw 66 (and thereby along axis 68) away from the corresponding syringe 86a/b. In this regard, the perimeter of at least part of the drive screw 66 includes helical threads 70 that interface with at least part of the ram 74. The ram 74 is also movably mounted within an appropriate bushing 78 that does not allow the ram 74 to rotate during a rotation of the drive screw 66. Therefore, the rotation of the drive screw 66 provides for an axial movement of the ram 74 in a direction determined by the rotational direction of the drive screw 66.

The ram 74 includes a coupler 76 that that may be detachably coupled with a syringe plunger coupler 94 of the syringe plunger 90a/b of the corresponding syringe 86a/b. When the ram coupler 76 and syringe plunger coupler 94 are appropriately coupled, the syringe plunger 90a/b moves along with ram 74. FIG. 2C illustrates a configuration where the syringe 86a/b may be moved along its corresponding axis 100a/b without being coupled to the ram 74. When the syringe 86a/b is moved along its corresponding axis 100a/b such that the head 96 of its syringe plunger 90a/b is aligned with the ram coupler 76, but with the axes 68 still in the offset configuration of FIG. 2C, the syringe 86a/b may be translated within a plane that is orthogonal to the axis 68 along which the ram 74 moves. This establishes a coupled engagement between the ram coupler 76 and the syringe plunger coupler 96 in the above-noted manner.

The power injectors 10, 40 of FIGS. 1 and 2A-C each may be used for any appropriate application, including without limitation for medical imaging applications where fluid is injected into a subject (e.g., a patient). Representative medical imaging applications for the power injectors 10, 40 include without limitation computed tomography or CT imaging, magnetic resonance imaging or MRI, SPECT imaging, PET imaging, X-ray imaging, angiographic imaging, optical imaging, and ultrasound imaging. The power injectors 10, 40 each could be used alone or in combination with one or more other components. The power injectors 10, 40 each may be operatively interconnected with one or more components, for instance so that information may be conveyed between the power injector 10, 40 and one or more other components (e.g., scan delay information, injection start signal, injection rate).

Any number of syringes may be utilized by each of the power injectors 10, 40, including without limitation single-head configurations (for a single syringe) and dual-head configurations (for two syringes). In the case of a multiple syringe configuration, each power injector 10, 40 may discharge fluid from the various syringes in any appropriate manner and according to any timing sequence (e.g., sequential discharges from two or more syringes, simultaneous discharges from two or more syringes, or any combination thereof). Each such syringe utilized by each of the power injectors 10, 40 may include any appropriate fluid, for instance contrast media, a radiopharmaceutical, or saline. Each such syringe utilized by each of the power injectors 10, 40 may be installed in any appropriate manner (e.g., rear-loading configurations may be utilized; front-loading configurations may be utilized).

Many applications, including without limitation various medical and veterinary procedures, require that one or more doses of a fluid be delivered to a subject or patient, or more generally a fluid target. FIG. 3A presents a perspective view of one embodiment of a fluid delivery system 300A that may be employed in such applications, or any other appropriate application. A fluid reservoir 302 is fluidly interconnectable with both a fluid target 318 and an injector 306a, where the injector 306a is in the form of a power injector. The fluid reservoir 302 may contain any appropriate fluid, including a single fluid or a combination of different fluids (e.g., contrast media, a radiopharmaceutical, saline, and any combination thereof). The fluid target 318 may be of any appropriate type (e.g., a patient, an animal). The fluid target 318 may receive fluid from the fluid reservoir 302 in any appropriate manner, including without limitation by injection in any appropriate manner. The power injector 306a may be of any appropriate size, shape, configuration, and/or type (e.g., at least generally in accordance with the discussion presented above regarding the power injector 10 of FIG. 1 and the power injector 40 of FIG. 2A), and includes a powerhead 310. Therefore, although the powerhead 310 is depicted with a single syringe 312, the injector 306a may be of a dual-head configuration (e.g., in accordance with the power injector 40 of FIG. 2A).

The fluid delivery system 300A includes what is commonly referred to as a "tubing set" or the like, which is identified by reference numeral 307. The tubing set 307 fluidly interconnects the fluid reservoir 302, the power injector 306a, and the fluid target 318. The tubing set 307 includes what may be characterized as a reusable section 309, as well as what may be characterized as a disposable section 308. The tubing set 307 may be of any appropriate size, shape, configuration, and/or type, may utilize any appropriate conduit or combination of conduits disposed in any appropriate arrangement, may incorporate one or more components in any appropriate manner and which provide any appropriate function or combination of functions, or any combination thereof.

One or more directional flow control devices 304 may be incorporated at any appropriate location throughout the tubing set 307. For instance, one or more directional flow control devices 304 may be employed to control fluid flow during loading of the syringe 312, during subsequent injection of the fluid into the fluid target 318, or both. Each of the directional flow control devices 304 utilized by the fluid delivery system 300A may be of any appropriate size, shape, configuration, and/or type. In one embodiment, the directional flow control devices 304 may be in the form of check valves oriented to reduce the potential for a backflow of fluid into the fluid reservoir 302 during injection or from the fluid target 318 during loading of the syringe 312.

Figure 3B:
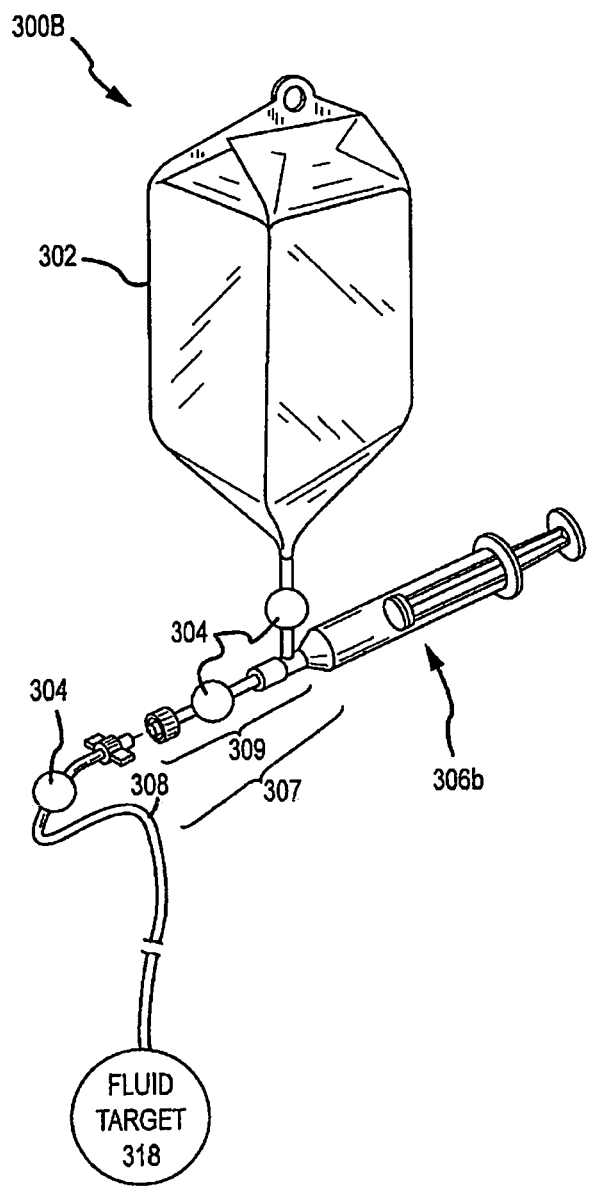
FIG. 3B is a perspective view of one embodiment of a fluid delivery system that utilizes a hand-activated syringe.

FIG. 3B is a perspective view of another embodiment of a fluid delivery system 300B having many of the same components just described, but having an injector 306b that is in the form of a hand-activated syringe. In these and other embodiments, fluid is retrieved from the fluid reservoir 302 and then provided to a fluid target 318 via the tubing set 307. Although the fluid reservoir 302 is depicted in FIGS. 3A-B as a discrete component, in other embodiments it may be in the form of a prefilled syringe or may otherwise be integrated with an injector of any appropriate type (e.g., injector 306a; syringe 306b). The fluid reservoir 302 may contain a standardized quantity of fluid, which may be more than the total amount required by a given fluid target 318.

The tubing set 307 used by each of the fluid delivery systems 300A and 300B of FIGS. 3A and 3B, respectively, again includes a disposable section 308 and a reusable section 309. Generally, one or more sterilization zones may be distributed throughout the tubing set 307 such that the reusable section 309 of the tubing set 307, as well as all upstream components of the respective fluid delivery system 300A, 300B, may be used to provide fluid to multiple fluid targets 318 (e.g., on a successive basis). This then allows the fluid reservoir 302 to contain multiple fluid doses. Various fluid delivery systems that incorporate at least one such sterilization zone will be addressed below in relation to FIGS. 4A-C. Various embodiments of sterilization systems that may be used in these sterilization zones will be addressed below in relation to FIGS. 5AD and 6-8. Without incorporating one or more sterilization zones in the fluid delivery systems 300A, 300B of FIGS. 3A-B, many fluid delivery system components would typically be changed and discarded on a per-fluid target 318 basis. This may include, for example, the entire tubing set 307, the fluid reservoir 302, the syringe 312 of FIG. 3A, and the injector/syringe 306b of FIG. 3B, along with other fluid path components that may be exposed to contaminants emanating from the fluid target 318. When the fluid reservoir 302 is discarded and replaced for successive fluid targets 318, any fluid remaining therein is typically wasted. In at least certain instances, the discarded fluid may be an expensive product (e.g., contrast media).

Figure 4A:
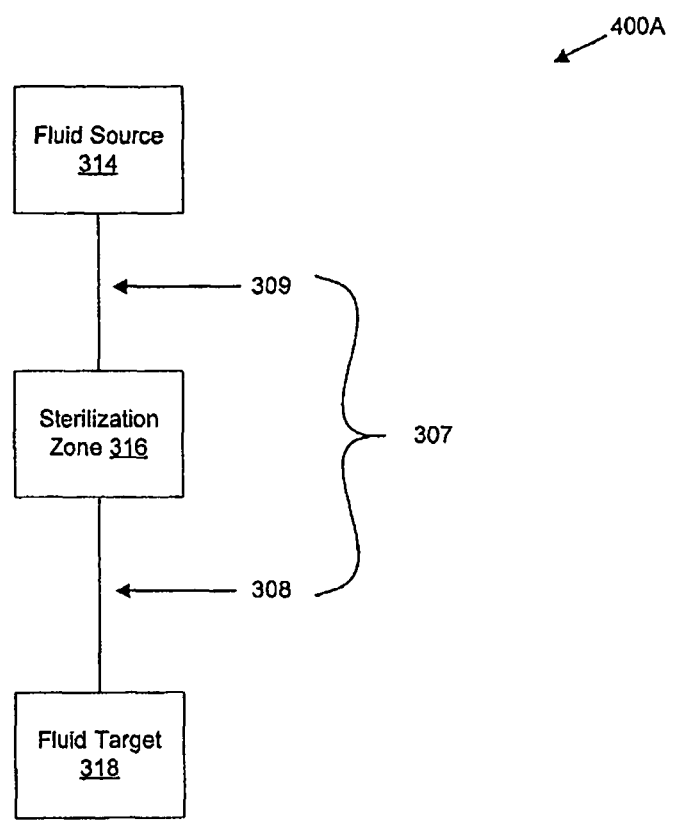
FIG. 4A is a schematic of one embodiment of a fluid delivery system that utilizes at least one sterilization zone.

FIG. 4A presents a schematic of one embodiment of a fluid delivery system 400A having a fluid source 314 fluidly interconnected by a tubing set 307 with at least one sterilization zone 316 and a fluid target 318. The fluid source 314 may be of any appropriate size, shape, configuration, and/or type. In various embodiments, the fluid source 314 may include a fluid reservoir, alone or in combination with a delivery device, where the delivery device includes an injector or other mechanism that may direct fluid through at least one sterilization zone 316 before reaching the fluid target 318. The fluid reservoir and delivery device may be discrete components, such as the fluid reservoir 302 and the injectors 306a, 306b of FIGS. 3A-B, or may be integrated into a single unit. Any separate fluid reservoir and delivery device may be disposed in any appropriate arrangement relative to a sterilization zone 316 and/or the fluid target 318. In various embodiments, the fluid delivery system 400A may include a plurality of fluid sources 314, sterilization zones 316, and/or fluid targets 318.

Any appropriate number of sterilization zones 316 may be utilized. In any case, the tubing set 307 has a disposable section 308 generally disposed between the fluid target 318 and at least one sterilization zone 316 (e.g., an adjacent-most sterilization zone 316), and a reusable section 309 generally disposed between the fluid source 314 and at least one sterilization zone 316 (e.g., an adjacent-most sterilization zone 316). Each sterilization zone 316 includes at least one sterilization system to reduce the potential for contaminants from the fluid target 318 flowing back through the tubing set 307 and reaching the fluid source 314, thus reducing waste by enabling the fluid source 314 to be reused for multiple fluid targets 318.

Figure 4B:
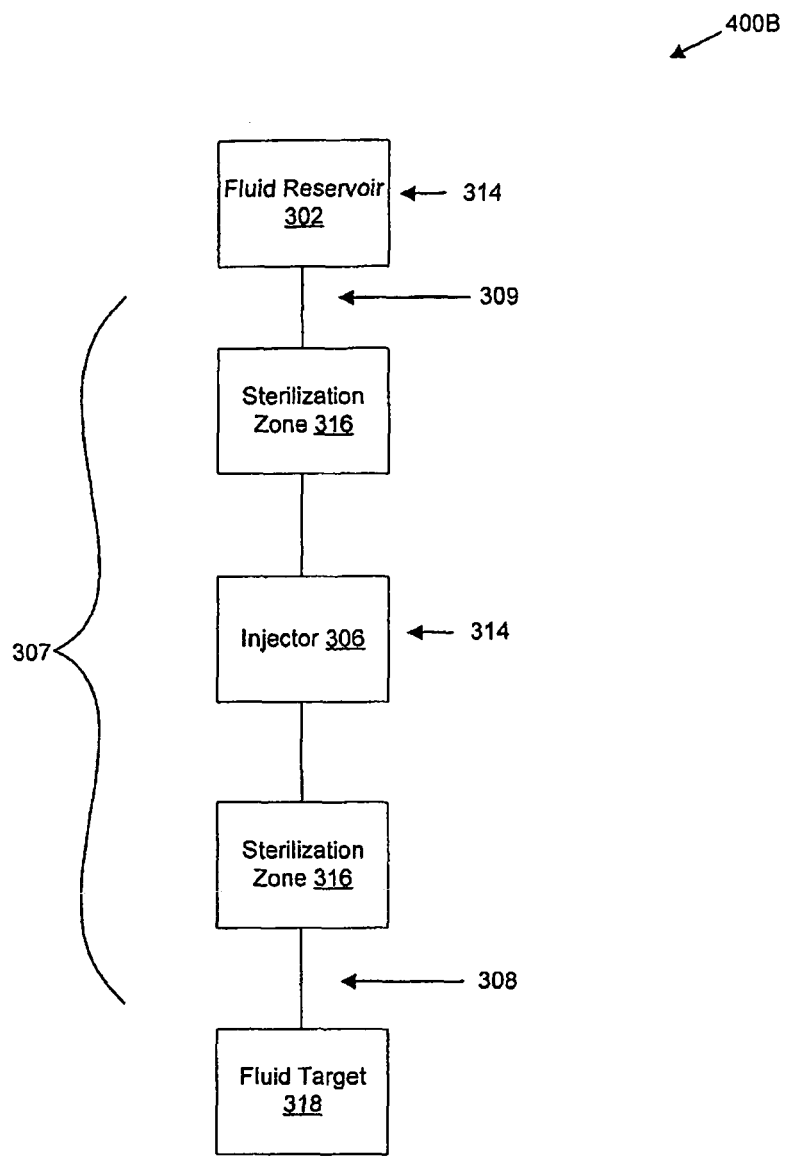
FIG. 4B is a schematic of another embodiment of a fluid delivery system that utilizes at least one sterilization zone, along with one arrangement of a fluid reservoir and injector.

FIG. 4B illustrates another embodiment of a fluid delivery system 400B having two fluid sources 314 fluidly interconnected with one or more sterilization zones 316 and a fluid target 318 by a tubing set 307. The tubing set 307 includes a disposable section 308 extending at least from the fluid target 318 to at least one sterilization zone 316 (e.g., an adjacent-most sterilization zone 316), as well as a reusable section 309 extending at least from one of the fluid sources 314 to at least one sterilization zone 316 (e.g., an adjacent-most sterilization zone 316). In one embodiment, the two fluid sources 314 include, respectively, a fluid reservoir 302 and an injector 306, where the injector 306 may be in the form of a power injector, a hand-activated syringe, or any other appropriate delivery device as described above. Fluid passes from the fluid reservoir 302 through at least one sterilization zone 316 (a single sterilization zone 316 in the illustrated embodiment) to reach the injector 306. The injector 306 then directs the fluid through at least one sterilization zone 316 (a single sterilization zone 316 and illustrated embodiment) to reach the fluid target 318. The fluid delivery system 400B may utilize any appropriate number of sterilization zones 316, including using only one of the sterilization zones 316. In any case, each sterilization zone 316 includes at least one sterilization system to reduce the potential for contaminants from the fluid target 318 flowing back through the tubing set 307 and reaching the fluid source 314 that includes the fluid reservoir 302, thus reducing waste by enabling the fluid reservoir 302 to be reused for multiple fluid targets. In embodiments utilizing a sterilization zone 316 between the injector 306 and the fluid target 318, components of the injector 306 may also be protected from contamination emanating from the fluid target 318.

Figure 4C:
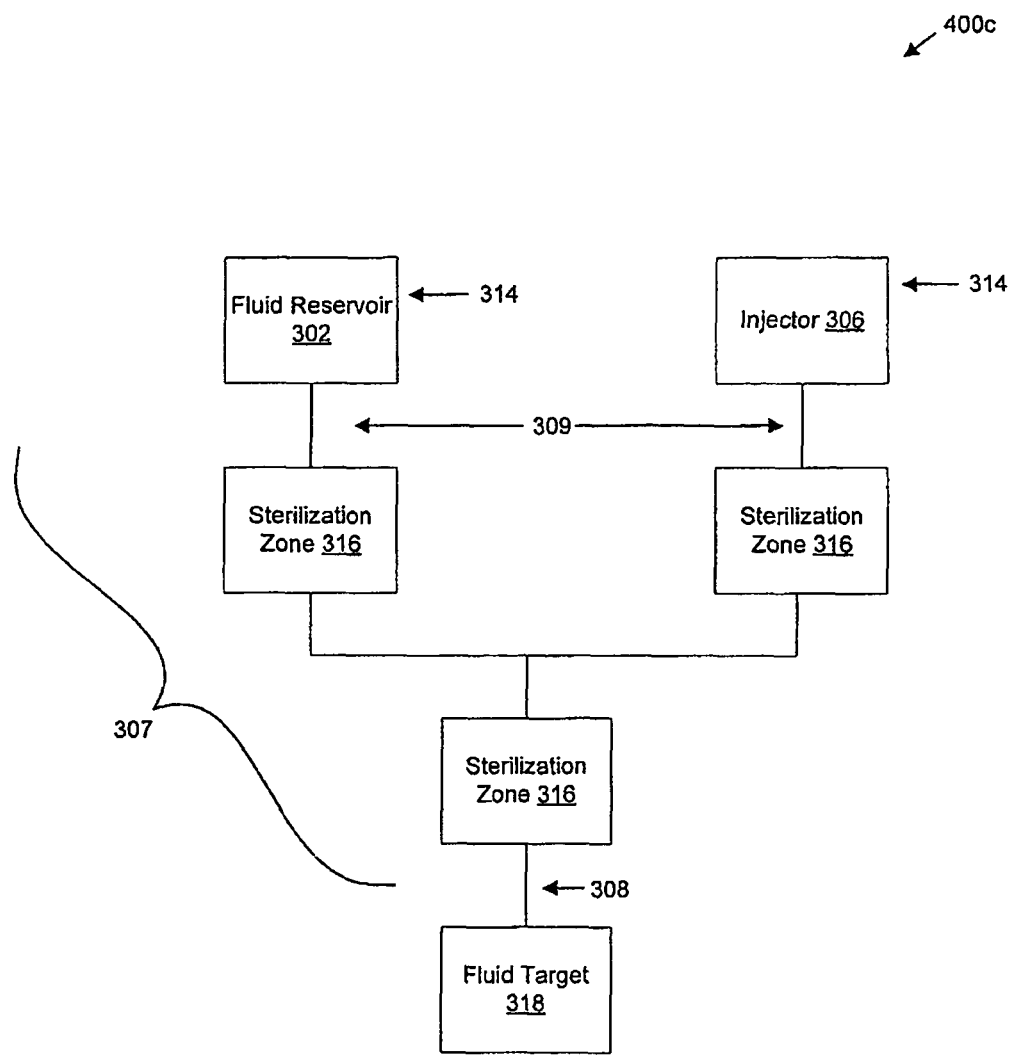
FIG. 4C is a schematic of another embodiment of a fluid delivery system that utilizes at least one sterilization zone, along with another arrangement of a fluid reservoir and injector.

FIG. 4C shows another embodiment of a fluid delivery system 400C having a fluid target 318 fluidly interconnected by a tubing set 307 to a plurality of fluid sources 314 and one or more sterilization zones 316, where each sterilization zone 316 includes at least one sterilization system as described above. The tubing set 307 again includes a disposable section 308 that extends at least from the fluid target 318 to at least one sterilization zone 316. The tubing set 307 also has one or more reusable sections 309, where each reusable section 309 extends from one of the fluid sources 314 at least as far as a sterilization zone 316 disposed between that fluid source 314 and the fluid target 318, if any. As in the fluid delivery system 400B of FIG. 4B, the fluid sources 314 may include, respectively, a fluid reservoir 302 and an injector 306. In a first stage, fluid may flow from the fluid reservoir 302 to the injector 306, optionally passing through one or more sterilization zones 316. In a next stage, fluid may flow from the injector 306 to the fluid target 318, optionally passing through one or more sterilization zones 316. Although the illustrated embodiment uses three sterilization zones 316, the fluid delivery system 400C may be adapted to include any appropriate number of sterilization zones (e.g., using only one or two of the sterilization zones 316). Depending on which of the sterilization zones 316 are included in the fluid delivery system 400C, one or both of the fluid sources 314 may be protected from contamination emanating from the fluid target 318.

Figure 5A:
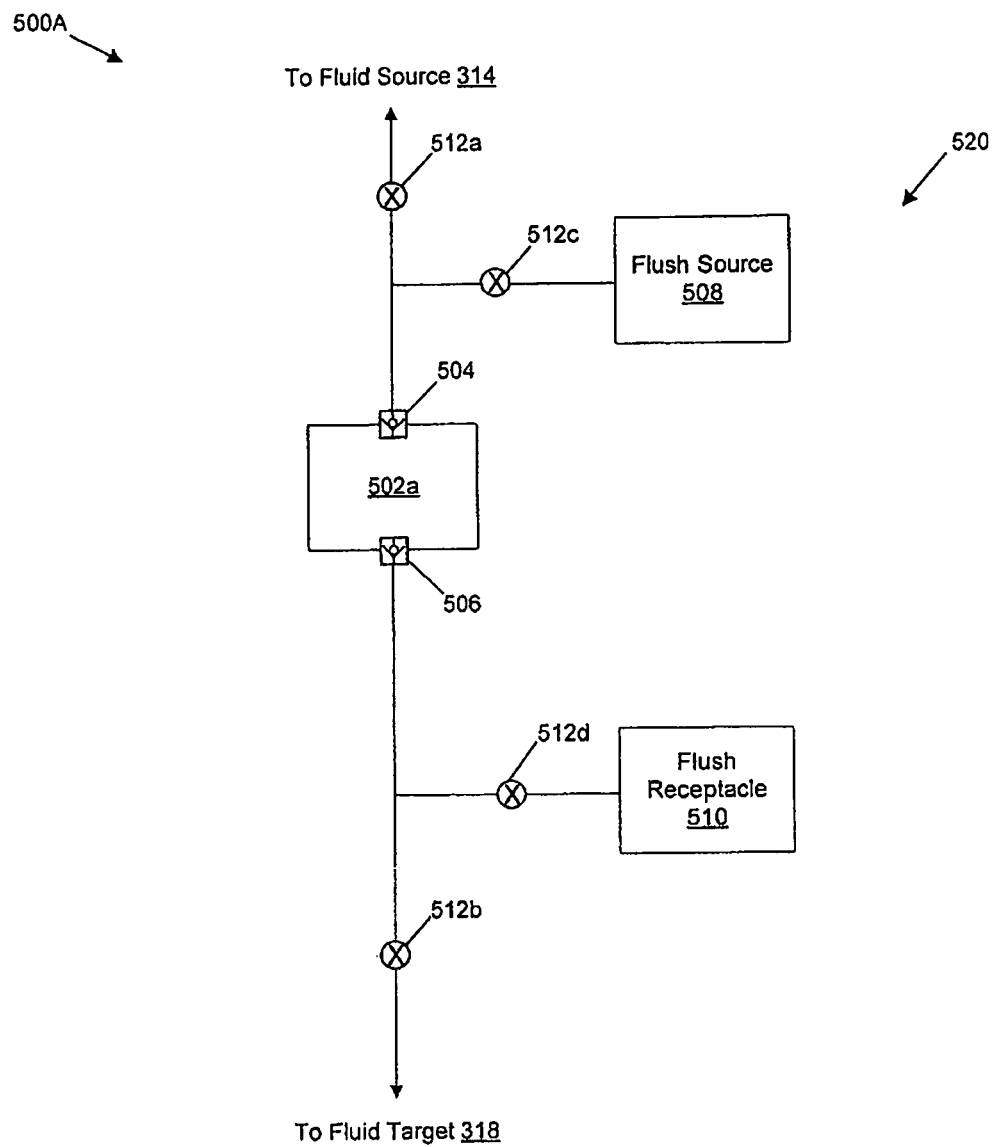
FIG. 5A is a schematic of one embodiment of a sterilization system that utilizes an intermediate chamber, and that may be incorporated into the fluid delivery system of FIGS. 4A-C.

FIGS. 5A-D illustrate various embodiments of a sterilization system that may be used by the fluid delivery systems 300A-B and 400A-C of FIGS. 3A-B and 4A-C described above, or any other appropriate fluid delivery system. Referring first to FIG. 5A, an intermediate chamber sterilization system 500A includes a flush system 520 and a container 502a. The flush system 520 includes both a flush source 508 and a flush receptacle 510 that are each fluidly interconnectable with the container 502a via a first inlet port 504 and a first outlet port 506, respectively. The flush source 508 may contain any appropriate flushing medium, including without limitation alcohol, steam, ETO, sterilizing fluid, water, air, an inert gas, a combination of inert gases, bleach, hydrogen peroxide, oxygen, any appropriate drying agent, and any combination thereof. The flush source 508 may utilize a single flushing medium or a combination of two or more different flushing mediums, which may be delivered by the flush source 508 in any appropriate manner and in any appropriate sequence. Each flushing medium may provide any appropriate function or combination of functions. Multiple flushing mediums may be directed through the container 502a on any appropriate basis.

The flush source 508 may be of any appropriate configuration to provide the functionality noted herein. The flush receptacle 510 also may be of any appropriate configuration, for instance in the form of a storage vessel or in the form of a waste drain or the like. The first inlet port 504 and/or the first outlet port 506 of the container 502a, as well as any additional ports, may be arranged to work passively, for example using a check valve system. Alternatively, they may utilize manually operated components such as push or twist ports, or employ solenoid valve actuation or some other automatic system. The ports 504, 506 of the container 502a, as well as any other container ports, need not incorporate any flow control functionality. Instead, flow control functionality may be provided by valving or the like incorporated into any conduit. The intermediate chamber sterilization system 500A may also use one or more flow regulators to facilitate fluidly interconnecting and disconnecting/isolating the container 502a with the flush source 508, the flush receptacle 510, a fluid source 314, and/or a fluid target 318. Each such flow regulator may be of any appropriate size, shape, configuration, and/or type, and may be designed to work passively, automatically, manually, based upon one or more signals, or using any combination of these methods.

During a fluid delivery stage in the case of the sterilization system 500A, the first inlet port 504 is fluidly interconnected with a fluid source 314 via a fluid source flow regulator 512a, and the first outlet port 506 is fluidly interconnected with a fluid target 318 via a fluid target flow regulator 512b. A flush source flow regulator 512c and a flush receptacle flow regulator 512d remain in a closed position such that the container 502a is fluidly disconnected or isolated from the flush source 508 and the flush receptacle 510. A first fluid quantity thereby may be directed from the fluid source 314 into the container 502a, after which at least part of the first fluid quantity may be directed from the container 502a to the fluid target 318.

After a desired amount of fluid has been delivered to the fluid target 318, the fluid flow to the fluid target 318 may be terminated in any appropriate manner (e.g., by the fluid target flow regulator 512b). Moreover, the fluid volume in the container 502a may be reduced, or the container 502a may be emptied of any remaining fluid, by reversing the direction of flow so as to return at least some of the remaining fluid to the fluid source 314. In embodiments employing this technique, it may be necessary to prevent backflow of fluid from the fluid target 318, which may be accomplished, for example, by closing the first outlet port 506 and/or the fluid target flow regulator 512b to fluidly disconnect or isolate the container 502a from the fluid target 318. Additionally or alternatively, the container 502a may be emptied by closing the fluid target flow regulator 512b or otherwise fluidly disconnecting or isolating the container 502a from the fluid target 318, opening the flush receptacle flow regulator 512d, and then bleeding off any remaining fluid through the first output port 506 into the flush receptacle 510. In another aspect, one or more flow regulators may be configured to fluidly disconnect or isolate the container 502a from the fluid source 314 and the fluid target 318 and to fluidly connect the container 502a to the flush source 508 and the flush receptacle 510. The container 502a may then be flushed by directing a flushing medium from the flush source 508 into the container 502a through the first inlet port 504, out of the container 502a through the first outlet port 506, and into the flush receptacle 510.

Figure 5B:
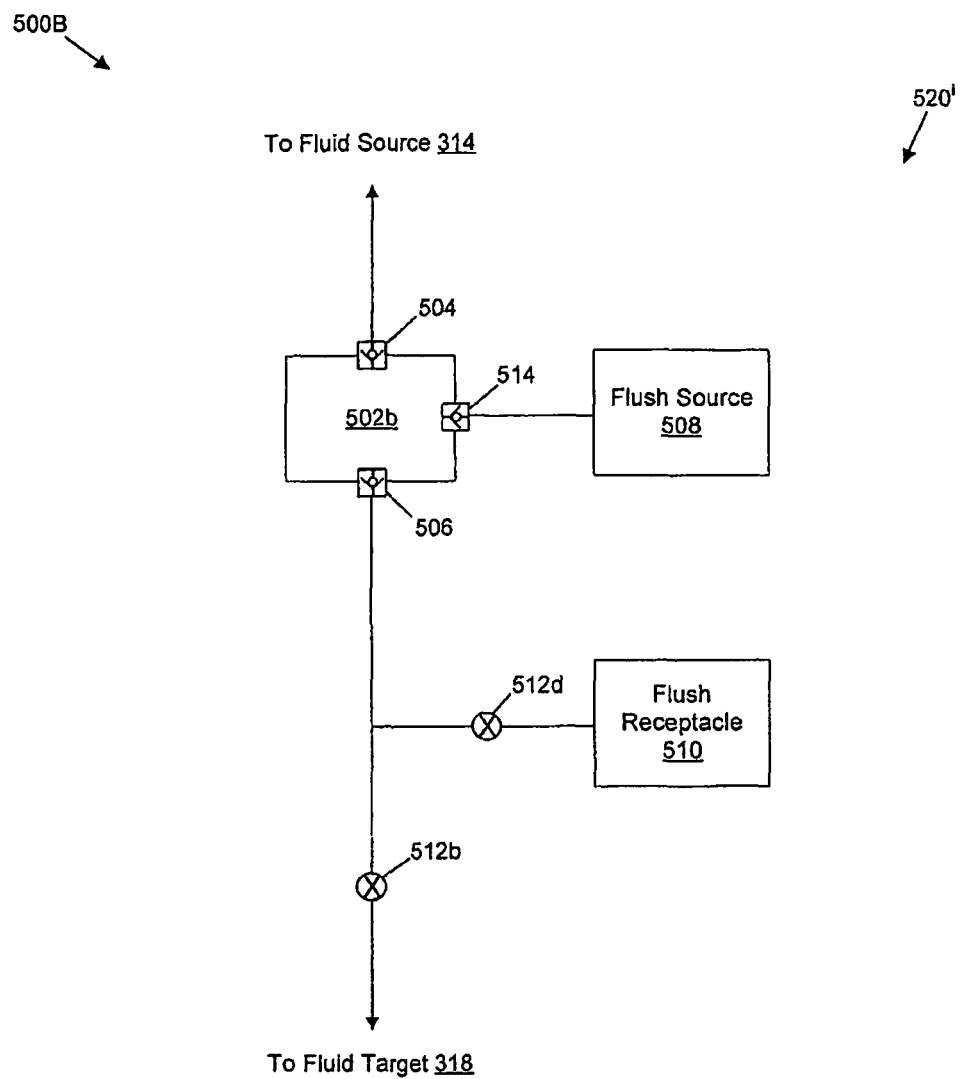
FIG. 5B is a schematic of another embodiment of a sterilization system that utilizes an intermediate chamber, and that may be incorporated in the fluid delivery system of FIGS. 4A-C.

Another embodiment of an intermediate chamber sterilization system 500B is depicted in FIG. 5B and includes a container 502b having all the features of the container 502a of FIG. 5A, plus a second inlet port 514. A flush system $520^i$ that includes a flush source 508 and flush receptacle 510 is fluidly connectable with the container 502b, although in a different arrangement from that presented in FIG. 5A (and thereby a superscripted "i" is utilized to identify the flush system $520^i$). The flush source 508 is fluidly interconnected with the second inlet port 514, which may eliminate the need to use one or more flow regulators to selectively interconnect the first inlet port 504 with one of the fluid source 314 and the flush source 508. While fluid is being delivered to the fluid target 318, the first inlet and outlet ports 504, 506 and the fluid target flow regulator 512b are open, while the second inlet port 514 and the flush receptacle flow regulator 512d remain closed. The container 502b may then be fluidly disconnected or isolated from the fluid target 318 by closing the first outlet port 506 and/or the fluid target flow regulator 512b, after which at least some of the remaining fluid in the container 502b may be emptied back into the fluid source 314 as described above. Additionally or alternatively, the container 502b may be emptied into the flush receptacle 510 after opening the first outlet port 506 and the flush receptacle flow regulator 512d and after closing the fluid target flow regulator 512b. Once flow leaving the container 502b via the first outlet port 506 is redirected from the fluid target 318 to the flush receptacle 510, and regardless of whether or by what method at least some of remaining fluid in container 502b is removed, the first inlet port 504 may be closed and the second inlet port 514 may be opened. The container 502b may then be sterilized by directing at least one flushing medium from the flush source 508 into the container 502b through the second inlet port 514, out of the container 502b through the first outlet port 506, and into the flush receptacle 510, at least generally in the manner discussed above regarding the FIG. 5A embodiment.

Figure 5C:
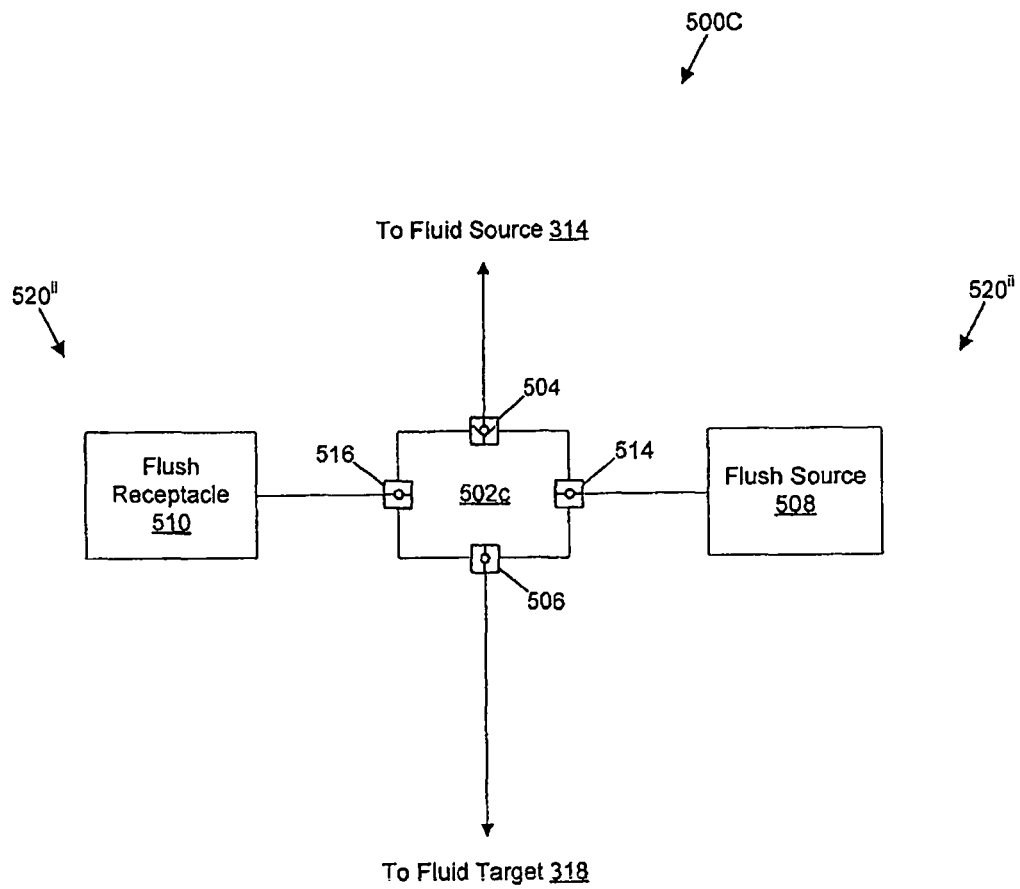
FIG. 5C is a schematic of another embodiment of a sterilization system that utilizes an intermediate chamber, and that may be incorporated in the fluid delivery system of FIGS. 4A-C.

In another embodiment, an intermediate chamber sterilization system 500C includes a container 502c having all the features of the container 502b of FIG. 5B, plus a second outlet port 516 as shown in FIG. 5C. A flush system $520^{ii}$ that includes a flush source 508 and flush receptacle 510 is fluidly connectable with the container 502c, although in a different arrangement from that presented in FIGS. 5A-B (and thereby a superscripted "ii" is utilized to identify the flush system $520^{ii}$). This configuration allows the container 502c to be in selective fluid communication either with the fluid source 314 and the fluid target 318, or with the flush source 508 and the flush receptacle 510, without the need for external flow regulators. After fluid has been delivered to the fluid target 318, the container 502c may be fluidly disconnected or isolated from the fluid target 318 in any appropriate manner. At least some of the remaining fluid in the container 502c may be removed and directed into the fluid source 314 as described above by first closing the second inlet port 514 (e.g., a flushing port) and the first and second outlet ports 506, 516 (e.g., the second outlet port 516 may be referred to as a flushing port) and opening the first inlet port 504. Additionally or alternatively, at least some of the remaining fluid in the container 502c may be directed into the flush receptacle after first closing the first inlet and outlet ports 504, 506 and opening the second outlet port 516. The container 502c may be flushed by further opening the second inlet port 514 and then directing at least one flushing medium from the flush source 508 into the container 502c through the second inlet port 514, out of the container 502c through the second outlet port 516, and into the flush receptacle 510 at least generally in the manner discussed above regarding the FIG. 5A embodiment.

Figure 5D:
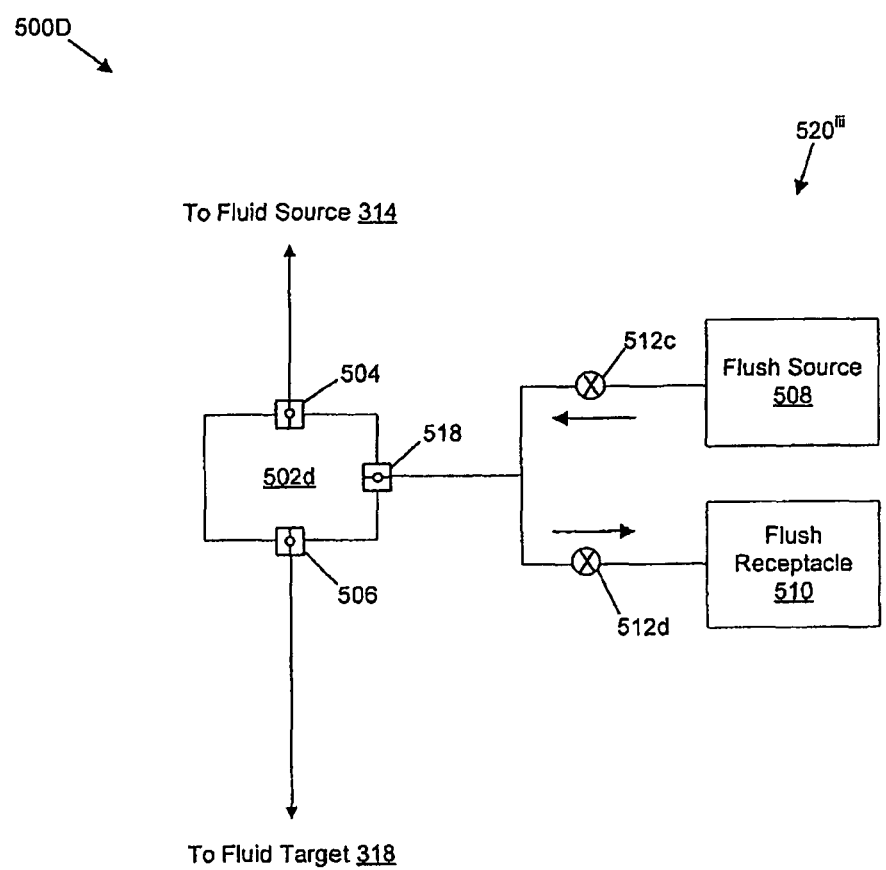
FIG. 5D is a schematic of another embodiment of a sterilization system that utilizes an intermediate chamber, and that may be incorporated in the fluid delivery system of FIGS. 4A-C.

FIG. 5D illustrates another embodiment of an intermediate chamber sterilization system 500D that includes a container 502d having a first inlet port 504, a first outlet port 506, and a flush port 518, where the flush port 518 is in selective fluid communication with a flush source 508 and a flush receptacle 510. A flush system $520^{iii}$ that includes a flush source 508 and flush receptacle 510 is fluidly connectable with the container 502d, although in a different arrangement from that presented in FIGS. 5A-C (and thereby a superscripted "iii" is utilized to identify the flush system 5209. After fluid has been delivered to the fluid target 318, the container 502d may be fluidly disconnected or isolated from the fluid target 318. At least some of the remaining fluid in the container 502d may then be removed by closing the flushing port 518 and the first outlet port 506 and then directing at least some of the remaining fluid back to the fluid source 314 through the first inlet port 504. Alternatively or additionally, at least some of the remaining fluid in the container 502d may be directed into the flush receptacle 510 through the flush port 518 after closing the first inlet and outlet ports 504, 506, closing the flush source flow regulator 512c, and opening the flush receptacle flow regulator 512d. Flushing the container 502d may involve directing at least one flushing medium from the flush source 508 into the container 502d through the flush port 518, and then removing this flushing medium from of the container 502d out through the same flush port 518 and directing the same to the flush receptacle 510. During this process, the flow regulators 512c, 512d may be alternately opened and closed to establish fluid communication between the flushing port 518 and the flush source 508 or the flush receptacle 510 as appropriate. Alternatively, the flow regulators 512c, 512d may be unidirectional in nature, such that each flow regulator 512c, 512d allows fluid to flow in only one direction as shown by the arrows in FIG. 5D.

Each of the ports for the containers 502a-d of FIGS. 5A-D may or may not incorporate flow control functionality (e.g., valving). Fluid disconnection or isolation of the various components noted in relation to the embodiments of FIGS. 5A-D may be realized in any appropriate manner, as may establishing a fluid communication between noted components. The flushing of each of the containers 502a-d may be repeated one or more times using a common or a combination of two or more flushing mediums. At least one flushing operation may provide a sterilization function for the relevant container 502a-d. For example, sterilizing the container 502a-d may include, without limitation, first flushing the container 502a-d with alcohol, next flushing the container 502a-d with water, and finally flushing the container 502a-d with an inert gas or other drying agent.

One or more intermediate chamber sterilization systems 500A-D may be located in any one or more of the sterilization zones 316 of the fluid delivery systems 400A-C described above. Thus, although the preceding discussion refers to fluidly interconnecting and fluidly disconnecting or isolating the container 502a-d to and from the fluid source 314 and the fluid target 318, it is understood that those connections may be indirect. For example, when an intermediate chamber sterilization system 500A-D is used in a sterilization zone 316 located between the two fluid sources 314 of the fluid delivery system 400B of FIG. 4B, it may be directly connected to the injector 306 and only indirectly connected to the fluid target 318.

Figure 6:
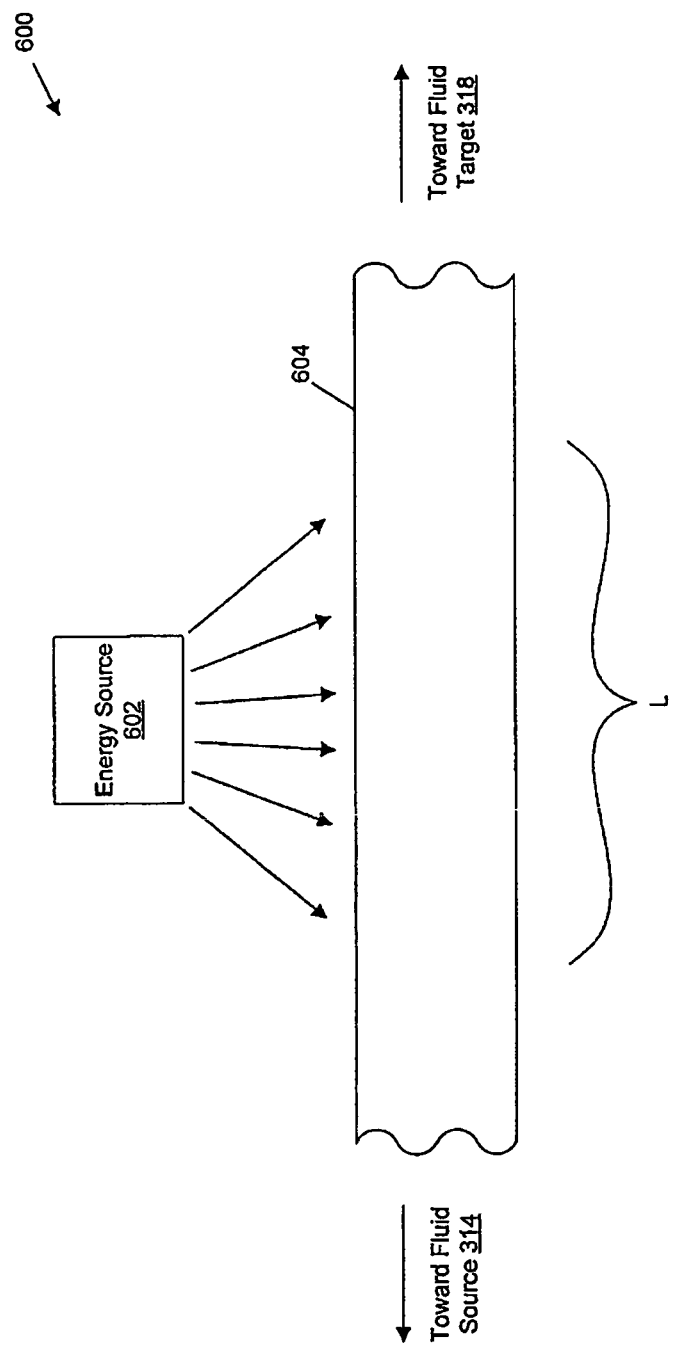
FIG. 6 is a schematic of one embodiment of a sterilization system that utilizes an energy source, and that may be incorporated in the fluid delivery system of FIGS. 4A-C.

FIG. 6 illustrates another embodiment of a sterilization system 600 that may be used by the fluid delivery systems 300A-B and 400A-C of FIGS. 3A-B and 4A-C described above, or any other appropriate fluid delivery system. The sterilization system 600 includes an energy source 602 and a flowpath 604, where at least part of the flowpath 604 having a length L may be exposed to an output of the energy source 602. The energy source 602 may include, without limitation, a source of heat, radiation, or other radiative energy capable of reducing a contamination level of a fluid in the flowpath 604 given a certain level of exposure, for instance by neutralizing and/or eliminating bacteria or other contamination present in a fluid passing through the flowpath 604 (e.g., heat, gamma radiation, ultraviolet radiation, infrared light, and any combination thereof). Reducing a contamination level may encompass exposing the fluid to a certain temperature or radiation dose for a specified exposure time, where the specified exposure time is at least long enough to ensure reduction of the contamination to a permissible level with an acceptable degree of certainty. The contamination may further have a maximum propagation speed at which it can diffuse through the fluid or otherwise spread to neighboring elements of substance. A minimum value for the length L can then be calculated by multiplying the maximum propagation speed of the contamination by the specified exposure time. Contamination entering the exposed portion of the flowpath 604 from the direction of the fluid target 318 should be prevented from propagating beyond the exposed portion in the direction of the fluid source 314. The sterilization system 600 may be utilized in one or more sterilization zones 316, such that fluid flowing between a fluid source 314 and a fluid target 318 passes through the flowpath 604 and is thereby exposed to the output of the energy source 602. In this way, contaminants entering the fluid delivery system 400A-C from the fluid target 318 should be prevented from infiltrating the fluid source 314.

Figure 7A:
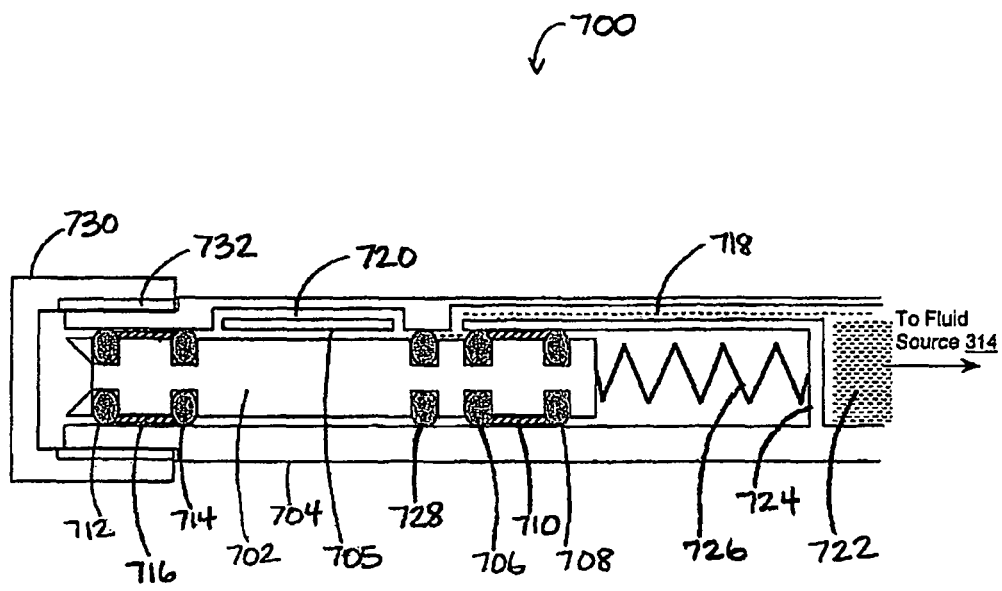
FIG. 7A is a schematic of one embodiment of a sterilization system that utilizes a self-sterilizing flow control device, and that may be incorporated in the fluid delivery system of FIGS. 4A-C.
Figure 7B:
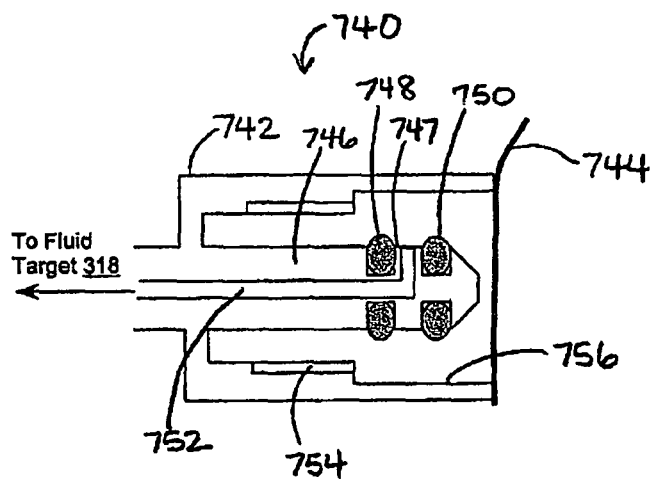
FIG. 7B is a schematic of one embodiment of a patient side connector for use in conjunction with the sterilization system of FIG. 7A.
Figure 7C:
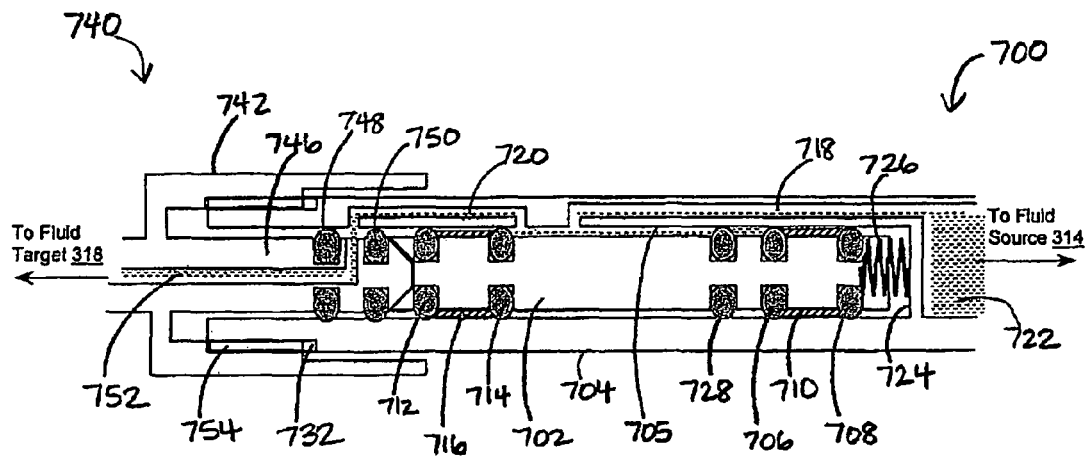
FIG. 7C shows the sterilization system of FIG. 7A with the patient side connector of FIG. 7B engaged.

FIGS. 7A-C present schematics (e.g., cutaway views) of another embodiment of a sterilization system that may be used by the fluid delivery systems 300A-B and 400A-C of FIGS. 3A-B and 4A-C described above, or any other appropriate fluid delivery system. A self-sterilizing flow control device 700 includes a plunger 702 movably disposed within a housing 704 having an interior surface 705. This interior surface 705 may define a conduit or flowpath for fluid flow, may interface with fluid within the flow control device 700, or both. First and second seals 706, 708 are mounted on and spaced along the plunger 702, and engage the interior surface 705 of the housing 704. A first sterilizing substance 710 is contained between the first and second seals 706, 708, such that any contaminants attempting to pass by the first and second seals 706, 708 encounter the first sterilizing substance 710. Additionally, third and fourth seals 712, 714 are mounted and spaced along the plunger 702 at some distance from the first and second seals 706, 708. A second sterilizing substance 716 may be disposed between the third and fourth seals 712, 714. The first and second sterilizing substances 710, 716 also engage the interior surface 705 of the housing 704, such that moving the plunger 702 within the housing 704 wipes the sterilizing substances 710, 716 along at least part of the interior surface 705 to treat contamination thereon. Each of the sterilizing substances 710, 716 may include, without limitation, a sterilizing liquid, a sterilizing gel, a sterilizing gas, and any combination thereof, or a sponge, cloth, a porous material, a hydrophilic material, and any combination thereof impregnated with any appropriate agent having suitable sterilizing properties.

The self-sterilizing flow control device 700 also has first and second flow passages 718, 720, where the first flow passage 718 may be fluidly interconnected with a fluid source 314. A fifth seal 728, mounted on the plunger 702 between a seal pair defined by the first and second seals 706, 708 and a seal pair defined by the third and fourth seals 712, 714, is situated so as to block fluid communication between the first and second flow passages 718, 720 when the plunger 702 is in a closed position, as illustrated in FIG. 7A. Thus, a fluid 722 entering the first flow passage 718 flows only as far as the fifth seal 728 with the self-sterilizing flow control device 700 being in its closed position. The self-sterilizing flow control device 700 also includes a biasing member 726 engaged between the plunger 702 and an end wall 724 of the housing 704, where the biasing member 726 biases the plunger 702 toward the closed position of FIG. 7A. Although the biasing member 726 is represented in FIG. 7A as a spring, it should be understood that any appropriate way of biasing the plunger 702 to the closed position of FIG. 7 may be utilized by the self-sterilizing flow control device 700 (e.g., using one or more biasing elements of any appropriate size, shape, configuration, and/or type).

The self-sterilizing flow control device 700 of FIG. 7A also includes a cap 730. The cap 730 is removably attached to an end of the housing 704. In one embodiment, the cap 730 screws onto helical threads 732 situated on the end of the housing 704. However, it should be understood that the cap 730 may removably interface with the housing 704 in any appropriate manner.

FIG. 7B is a schematic (e.g., a cutaway view) of a fluid target side connector 740 for use in conjunction with the self-sterilizing flow control device 700 of FIG. 7A. A connector housing 742 contains a first member 746 on which are mounted sixth and seventh seals 748, 750. A third flow passage 752 intersects a sidewall 747 of the first member 746 between the sixth and seventh seals 748, 750 and extends through the first member 746, such that the third flow passage 752 may be fluidly interconnected with a fluid target 318. A protective cover 744 is removably attached to an end of the connector housing 742, where the protective cover 744 may be implemented as a peel-off cover or any other suitable covering. Any way of removably attaching the protective cover 744 to the connector housing 742 may be utilized. The target side connector 740 may also have helical threads 754 situated on an interior wall 756 of the connector housing 742 to threadably engage with the helical threads 732 on the end of the housing 704. However, any appropriate way of coupling the fluid target side connector 740 to the self-sterilizing flow control device 700 may be utilized.

After the protective cover 744 has been removed from the connector housing 742 (FIG. 7B), and after the cap 730 has been removed from the housing 704 of the self-sterilizing flow control device 700 (FIG. 7A), the fluid target side connector 740 may be interconnected with the self-sterilizing flow control device 700 as shown in FIG. 7C. Coupling the fluid target side connector 740 with the self-sterilizing flow control device 700 causes the first member 746 of the fluid target side connector 740 to engage the plunger 702 of the self-sterilizing flow control device 700 and push it away from the closed position of FIG. 7A, thereby wiping the sterilizing substances 710, 716 along portions of the interior surface 705 to treat any contamination thereon before fluid is delivered to the fluid target 318. Once the fluid target side connector 740 is fully engaged with the self-sterilizing flow control device 700, the plunger 702 is disposed in its open position of FIG. 7C, such that the fifth seal 728 no longer blocks fluid communication between the first and second flow passages 718, 720 of the self-sterilizing flow control device 700. Additionally, the third flow passage 752 of the fluid target side connector 740 is now aligned with the second flow passage 720 of the self-sterilizing flow control device 700, such that the first, second, and third flow passages 718, 720, 752 form a continuous flowpath 758. The sixth and seventh seals 748, 750 of the fluid target side connector 740 engage the interior surface 705 of the housing 704 of the self-sterilizing flow control device 700 to guide fluid into the third flow passage 752 of the fluid target side connector 740. In this way, a fluid 722 entering the self-sterilizing flow control device 700 from the fluid source 314 may flow through the continuous flowpath 758 toward the fluid target 318.

Once or after a desired amount of fluid has been delivered to the fluid target 318, the fluid target side connector 740 may be disconnected from the self-sterilizing flow control device 700. Removing the target side connector 740 allows the biasing member 726 to move the plunger 702 back to the closed position illustrated in FIG. 7A. This motion of the plunger 702 in turn causes the sterilizing substances 710, 716 to again be wiped along portions of the interior surface 705 of the housing 704, thereby treating any contamination left on the interior surface 705 after delivering fluid to the fluid target 318.

Figure 8:
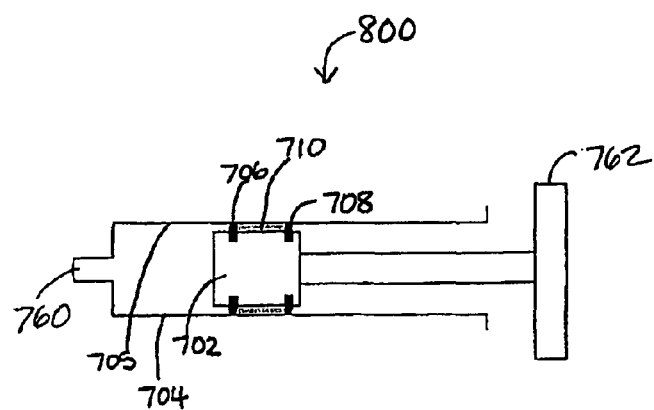
FIG. 8 is a schematic of another embodiment of a sterilization system that utilizes a self-sterilizing flow control device, and that may be incorporated in the fluid delivery system of FIGS. 4A-C.

FIG. 8 is a schematic (e.g., cutaway view) of another embodiment of a self-sterilizing flow control device 800 that at least generally utilizes at least part of the sterilizing principles of the self-sterilizing flow control device 700 of FIGS. 7A-C. Corresponding components between the embodiments of FIGS. 7A-C and FIG. 8 are identified by the same reference numeral. Those corresponding components that differ in at least some respect are further identified by a "single prime" designation. The self-sterilizing flow control device 800 includes a plunger 702' movably disposed within a housing 704' having an interior surface 705'. First and second seals 706, 708 are mounted on and spaced along the plunger 702' and engage the interior surface 705' of the housing 704'. A sterilizing substance 710 is contained between the first and second seals 706, 708, such that any contaminants attempting to pass by the first and second seals 706, 708 encounter the sterilizing substance 710. The sterilizing substance 710 also engages the interior surface 705' of the housing 704', such that moving the plunger 702' within the housing 704' wipes the sterilizing substance 710 along at least part of the interior surface 705' to treat contamination thereon.

In the illustrated embodiment, the self-sterilizing flow control device 800 is generally configured as a syringe, where the housing 704' forms the barrel of the syringe and further includes a nozzle 760. The plunger 702' may extend beyond an end of the housing 704' and may include without limitation a handle 762 for manually advancing the plunger 702'. Alternatively, the plunger 702' may include any means of coupling the plunger 702' to a power injector, such as by including the syringe plunger coupler 94 of FIGS. 2B-C. Loading the self-sterilizing flow control device 800 may involve retracting the plunger 702 to draw or otherwise allow fluid to flow into the housing 704' through the nozzle 760, while discharging the self-sterilizing flow control device 800 includes advancing the plunger 702 to expel fluid through the nozzle 760. Thus, at least a portion of the interior surface 705' of the housing 704' undergoes a sterilizing treatment before and/or after every injection through advancement of the plunger 702'.

Each of the sterilization systems 500A-D, 600, 700, and 800 of FIGS. 5A-8, or any combination thereof, may be incorporated into the fluid delivery systems 300A-B and 400A-C of FIGS. 3A-B and 4A-C, respectively, or any other fluid delivery system as appropriate to reduce potential back-contamination from a fluid target 318 to one or more fluid sources 314. Furthermore, elements of the sterilization systems described above may be combined to create other embodiments; for example, the energy source 602 of FIG. 6 may be configured to interface with any of the containers 502a-d of the intermediate chamber sterilization systems 500A-D of FIGS. 5A-D as an additional or alternative method of reducing contamination inside the container 502a-d. In any case, fluid is provided to the fluid target 318 with less risk of contaminants infiltrating a fluid source 314, such that the fluid source 314 may be reused for subsequent fluid targets 318. Other fluid delivery components located opposite a sterilization zone 316 from the fluid target 318, such as a reusable section 309 of a tubing set 307, may also be sufficiently protected from contamination to be reused for successive fluid targets 318. Some of the many resulting advantages may include reduced packaging costs, quicker procedure times when fewer parts are replaced between successive fluid targets 318, reduced fluid waste, and safer delivery of high-value or high-purity substances.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed is:

1. A fluid delivery system, comprising:
a fluid reservoir comprising fluid for multiple fluid targets;
a first flowpath extending from said fluid reservoir to a first fluid target;
an injector fluidly interconnected with said first flowpath, wherein said first flowpath comprises first and second conduit sections that comprise first and second connectors, respectively, wherein engaging said first connector with said second connector detachably connects said first and second conduit sections together, wherein said first conduit section extends from said second conduit section to said first fluid target and is disposable, wherein each of said fluid reservoir and said injector discharge directly into said second conduit section, wherein a discharge from said injector is directed into said second conduit section, then proceeds through said first conduit section, and then reaches said first fluid target, wherein said second conduit section is reusable for multiple fluid targets by disconnecting said first conduit section from said second conduit section by disengaging said first connector from said second connector, and wherein said injector comprises a syringe that is fluidly connectable with said fluid reservoir by said second conduit section for loading some of said fluid from said fluid reservoir into said syringe for subsequent delivery to a fluid target;
a first check valve within said second conduit section so as to be located between said first conduit section and each of said fluid reservoir and said injector;
an energy source that provides an output comprising radiative energy of at least one wavelength, wherein at least about 13 centimeters of said first flowpath is exposed to said output from said energy source and comprising at least part of said first conduit section, wherein said energy source is operated to at least one of neutralize and eliminate bacteria to reduce a potential of contaminants migrating from said first fluid target, through said first conduit section, then into said second conduit section, and then back to each of said fluid reservoir and said injector.

2. The fluid delivery system of claim 1, wherein said fluid reservoir comprises contrast media.

3. The fluid delivery system of claim 1, wherein said fluid reservoir comprises a quantity of fluid for accommodating multiple fluid delivery procedures.

4. The fluid delivery system of claim 1, wherein said first flowpath comprises at least one conduit.

5. The fluid delivery system of claim 1, wherein said injector comprises a power injector.

6. The fluid delivery system of claim 1, wherein said injector comprises a hand-activated syringe.

7. The fluid delivery system of claim 1, wherein said first check valve allows flow in a direction of said first conduit section, and wherein said first conduit section comprises a check valve that allows a flow from said second conduit section to proceed through said first conduit section to reach said first fluid target.

8. The fluid delivery system of claim 1, wherein said output of said energy source travels through an open space to reach said first conduit section.

9. The fluid delivery system of claim 1, wherein said first check valve allows flow in a direction of said first conduit section.

10. The fluid delivery system of claim 1, wherein said second conduit section comprises a second check valve.

11. The fluid delivery system of claim 10, wherein a flow out of said fluid reservoir is first directed through said second check valve and then through said first check valve, and wherein a flow out of each of said fluid reservoir and said injector is directed through said first check valve to reach said first conduit section.

12. The fluid delivery system of claim 11, wherein a flow out of said injector into said second conduit section is blocked from reaching said fluid reservoir by said second check valve.

13. The fluid delivery system of claim 10, wherein said first conduit section comprises a third check valve, wherein said third check valve allows a flow from said second conduit section to proceed through said first conduit section to reach said first fluid target.

14. The fluid delivery system of claim 13, wherein a flow out of said fluid reservoir is first directed through said second check valve and then through said first check valve, and wherein a flow out of each of said fluid reservoir and said injector is directed through said first check valve to reach said first conduit section.

15. The fluid delivery system of claim 14, wherein a flow out of said injector into said second conduit section is blocked from reaching said fluid reservoir by said second check valve.

16. A fluid delivery system, comprising:
a fluid reservoir comprising fluid for multiple fluid targets;
a first flowpath extending from said fluid reservoir to a first fluid target;
an injector fluidly interconnected with said first flowpath, wherein said first flowpath comprises first and second conduit sections that each comprise a connector for detachably connecting said first and second conduit sections together, wherein said first conduit section extends from said second conduit section to said first fluid target and is disposable, wherein each of said fluid reservoir and said injector discharge directly into said second conduit section, wherein a discharge from said injector is directed into said second conduit section, then proceeds through said first conduit section, and then reaches said first fluid target, wherein said second conduit section is reusable for multiple fluid targets, and wherein said injector comprises a syringe that is fluidly connectable with said fluid reservoir by said second conduit section for loading some of said fluid from said fluid reservoir into said syringe for subsequent delivery to a fluid target;
a first check valve within said second conduit section so as to be located between said first conduit section and each of said fluid reservoir and said injector, wherein said second conduit section comprises a second check valve; and
an energy source, wherein at least part of said first conduit section is exposed to an output of said energy source, which is operable to reduce a potential of contaminants migrating from said first fluid target, through said first conduit section, then into said second conduit section, and then back to each of said fluid reservoir and said injector, wherein said first conduit section comprises a third check valve, wherein said third check valve allows a flow from said second conduit section to proceed through said first conduit section to reach said first fluid target.

17. A fluid delivery system, comprising:
a fluid reservoir comprising fluid for multiple fluid targets;
a first flowpath extending from said fluid reservoir to a first fluid target;
an injector fluidly interconnected with said first flowpath, wherein said first flowpath comprises first and second conduit sections that each comprise a connector for detachably connecting said first and second conduit sections together, wherein said first conduit section extends from said second conduit section to said first fluid target and is disposable, wherein each of said fluid reservoir and said injector discharge directly into said second conduit section, wherein a discharge from said injector is directed into said second conduit section, then proceeds through said first conduit section, and then reaches said first fluid target, wherein said second conduit section is reusable for multiple fluid targets, and wherein said injector comprises a syringe that is fluidly connectable with said fluid reservoir by said second conduit section for loading some of said fluid from said fluid reservoir into said syringe for subsequent delivery to a fluid target;
a first check valve within said second conduit section so as to be located between said first conduit section and each of said fluid reservoir and said injector, wherein said first check valve allows flow in a direction of said first conduit section, and wherein said first conduit section comprises a check valve that allows a flow from said second conduit section to proceed through said first conduit section to reach said first fluid target; and
an energy source, wherein at least part of said first conduit section is exposed to an output of said energy source, which is operable to reduce a potential of contaminants migrating from said first fluid target, through said first conduit section, then into said second conduit section, and then back to each of said fluid reservoir and said injector.

* * * * *